United States Patent
Sampath et al.

(10) Patent No.: US 8,088,582 B2
(45) Date of Patent: Jan. 3, 2012

(54) COMPOSITIONS FOR THE USE IN IDENTIFICATION OF FUNGI

(75) Inventors: Rangarajan Sampath, San Diego, CA (US); Thomas A. Hall, Oceanside, CA (US); David J. Ecker, Encinitas, CA (US)

(73) Assignee: Ibis Biosciences, Inc., Carlsbad, CA (US)

( * ) Notice: Subject to any disclaimer, the term of this patent is extended or adjusted under 35 U.S.C. 154(b) by 298 days.

(21) Appl. No.: 12/296,253

(22) PCT Filed: Apr. 6, 2007

(86) PCT No.: PCT/US2007/066194
§ 371 (c)(1),
(2), (4) Date: Feb. 20, 2009

(87) PCT Pub. No.: WO2007/118222
PCT Pub. Date: Oct. 18, 2007

(65) Prior Publication Data
US 2009/0311683 A1 Dec. 17, 2009

Related U.S. Application Data

(60) Provisional application No. 60/790,499, filed on Apr. 6, 2006.

(51) Int. Cl.
*C12Q 1/70* (2006.01)
*C07H 21/04* (2006.01)
(52) U.S. Cl. .................... 435/6.12; 536/24.3
(58) Field of Classification Search .................... None
See application file for complete search history.

(56) References Cited

U.S. PATENT DOCUMENTS

| | | |
|---|---|---|
| 5,436,129 A | 7/1995 | Stapleton |
| 5,451,500 A | 9/1995 | Stapleton |
| 5,484,908 A | 1/1996 | Froehler et al. |
| 5,523,217 A | 6/1996 | Lupski et al. |
| 5,547,835 A | 8/1996 | Koster |
| 5,567,587 A | 10/1996 | Kohne |
| 5,605,798 A | 2/1997 | Koster |
| 5,622,824 A | 4/1997 | Koster |
| 5,683,869 A | 11/1997 | Ramsay Shaw et al. |
| 5,691,141 A | 11/1997 | Koster |
| 5,707,802 A | 1/1998 | Sandhu et al. |
| 5,727,202 A | 3/1998 | Kucala |
| 5,745,751 A | 4/1998 | Nelson et al. |
| 5,759,771 A | 6/1998 | Tilanus |
| 5,763,169 A | 6/1998 | Sandhu et al. |
| 5,777,324 A | 7/1998 | Hillenkamp |
| 5,832,489 A | 11/1998 | Kucala |
| 5,849,492 A | 12/1998 | Rogan |
| 5,849,901 A | 12/1998 | Mabilat et al. |
| 5,851,765 A | 12/1998 | Koster |
| 5,871,697 A | 2/1999 | Rothberg et al. |
| 5,872,003 A | 2/1999 | Koster |
| 5,900,481 A | 5/1999 | Lough et al. |
| 5,928,906 A | 7/1999 | Koster et al. |
| 5,965,363 A | 10/1999 | Monforte et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 6,001,564 A | 12/1999 | Bergeron et al. |
| 6,018,713 A | 1/2000 | Coli et al. |
| 6,024,925 A | 2/2000 | Little et al. |
| 6,043,031 A | 3/2000 | Koster et al. |
| 6,051,378 A | 4/2000 | Monforte et al. |
| 6,055,487 A | 4/2000 | Margery et al. |
| 6,060,246 A | 5/2000 | Summerton et al. |
| 6,061,686 A | 5/2000 | Gauvin et al. |
| 6,074,823 A | 6/2000 | Koster |
| 6,074,831 A | 6/2000 | Yakhini et al. |
| 6,090,558 A | 7/2000 | Butler et al. |
| 6,111,251 A | 8/2000 | Hillenkamp |
| 6,133,436 A | 10/2000 | Koster et al. |
| 6,140,053 A | 10/2000 | Koster |
| 6,146,854 A | 11/2000 | Koster et al. |
| 6,180,339 B1 | 1/2001 | Sandhu et al. |
| 6,180,372 B1 | 1/2001 | Franzen |
| 6,194,144 B1 | 2/2001 | Koster |
| 6,197,498 B1 | 3/2001 | Koster |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,478 B1 | 5/2001 | Koster |

(Continued)

FOREIGN PATENT DOCUMENTS

DE 19802905 A1 7/1999
(Continued)

OTHER PUBLICATIONS

Magnuson et al., Substrate Nucleotide-Determined Non-Templated Addition of Adenine by TaqDNA Polymerase: Implications for PCR-Based Genotyping and Cloning, BioTechniques 21:700-709 (Oct. 1996).*
Buck et al., Design Strategies and Performance of Custom DNA Sequencing Primers, BioTechniques 27:528-536 (Sep. 1999).*
Dieckmann et al., Rapid screening and dereplication of bacterial isolate from marine sponges of the Sula Ridge by Intact-Cell-MALDI-TOF mass spectrometry (ICM-MS), Appl Microbiol Biotechnol (2005) 67: 539-548.*
Gen Bank, Accession No. X70659.1, 1996, pp. 1-2, acessessed through: http://www.ncbi.nlm.nih.gov/nucleotide.*
Aaserud D.J., et al., "Accurate Base Composition of Double-Strand DNA by Mass Spectrometry," American Society for Mass Spectrometry, 1996, vol. 7 (12), pp. 1266-1269.
Alves-Silva J., et al., "The Ancestry of Brazilian mtDNA Linages," The American Journal of Human Genetics, 2000, vol. 67 (2), pp. 444-461.
Anderson S., et al., "Sequence and Organization of the Human Mitochondrial Genome," Nature, 1981, vol. 290 (5806), pp. 457-465.
Andreasson H., et al., "Mitochondrial Sequence Analysis for Forensic Identification Using Pyrosequencing Technology," BioTechniques, 2002, vol. 32 (1), pp. 124-133.

(Continued)

*Primary Examiner* — Mark Staples
(74) *Attorney, Agent, or Firm* — Casimir Jones S.C.; Christopher C. Sappenfield

(57) ABSTRACT

The present invention provides compositions, kits and methods for rapid identification and quantification of fungi by molecular mass and base composition analysis.

27 Claims, 4 Drawing Sheets

U.S. PATENT DOCUMENTS

| | | | |
|---|---|---|---|
| 6,238,871 B1 | 5/2001 | Koster | |
| 6,258,538 B1 | 7/2001 | Koster et al. | |
| 6,268,131 B1 | 7/2001 | Kang et al. | |
| 6,268,144 B1 | 7/2001 | Koster | |
| 6,277,573 B1 | 8/2001 | Koster | |
| 6,300,076 B1 | 10/2001 | Koster | |
| 6,303,297 B1 | 10/2001 | Lincoln et al. | |
| 6,322,970 B1 | 11/2001 | Little et al. | |
| 6,389,428 B1 | 5/2002 | Rigault et al. | |
| 6,393,367 B1 | 5/2002 | Tang et al. | |
| 6,419,932 B1 | 7/2002 | Dale | |
| 6,423,966 B2 | 7/2002 | Hillenkamp et al. | |
| 6,428,955 B1 | 8/2002 | Koster et al. | |
| 6,436,635 B1 | 8/2002 | Fu et al. | |
| 6,453,244 B1 | 9/2002 | Oefner | |
| 6,468,743 B1 | 10/2002 | Romick et al. | |
| 6,468,748 B1 | 10/2002 | Monforte et al. | |
| 6,475,143 B2 | 11/2002 | Iliff | |
| 6,500,621 B2 | 12/2002 | Koster | |
| 6,553,317 B1 | 4/2003 | Lincoln et al. | |
| 6,558,902 B1 | 5/2003 | Hillenkamp | |
| 6,566,055 B1 | 5/2003 | Monforte et al. | |
| 6,589,485 B2 | 7/2003 | Koster | |
| 6,602,662 B1 | 8/2003 | Koster et al. | |
| 6,605,433 B1 | 8/2003 | Fliss et al. | |
| 6,613,520 B2 | 9/2003 | Ashby | |
| 6,680,476 B1 | 1/2004 | Hidalgo et al. | |
| 6,706,530 B2 | 3/2004 | Hillenkamp | |
| 7,108,974 B2 | 9/2006 | Ecker et al. | |
| 7,198,893 B1 | 4/2007 | Köster et al. | |
| 7,217,510 B2 | 5/2007 | Ecker et al. | |
| 7,226,739 B2 | 6/2007 | Ecker et al. | |
| 7,255,992 B2 | 8/2007 | Ecker et al. | |
| 7,285,422 B1 | 10/2007 | Little et al. | |
| 7,419,787 B2 | 9/2008 | Köster | |
| 7,501,251 B2 | 3/2009 | Köster et al. | |
| 7,741,036 B2 | 6/2010 | Ecker et al. | |
| 2002/0042112 A1 | 4/2002 | Koster et al. | |
| 2002/0055101 A1 | 5/2002 | Bergeron et al. | |
| 2002/0138210 A1 | 9/2002 | Wilkes et al. | |
| 2002/0168630 A1 | 11/2002 | Fleming et al. | |
| 2003/0027135 A1 | 2/2003 | Ecker et al. | |
| 2003/0039976 A1* | 2/2003 | Haff | 435/6 |
| 2003/0113745 A1 | 6/2003 | Monforte et al. | |
| 2003/0129589 A1 | 7/2003 | Koster et al. | |
| 2003/0175695 A1 | 9/2003 | Ecker et al. | |
| 2003/0175696 A1 | 9/2003 | Ecker et al. | |
| 2003/0175697 A1 | 9/2003 | Ecker et al. | |
| 2003/0190605 A1 | 10/2003 | Ecker et al. | |
| 2003/0224377 A1* | 12/2003 | Wengel et al. | 435/6 |
| 2003/0228597 A1 | 12/2003 | Cowsert et al. | |
| 2004/0081993 A1 | 4/2004 | Cantor et al. | |
| 2004/0110169 A1 | 6/2004 | Ecker et al. | |
| 2004/0202997 A1 | 10/2004 | Ecker et al. | |
| 2009/0042203 A1 | 2/2009 | Koster | |
| 2009/0092977 A1 | 4/2009 | Koster | |

FOREIGN PATENT DOCUMENTS

| | | | |
|---|---|---|---|
| DE | 19824280 A1 | 12/1999 | |
| DE | 19852167 A1 | 5/2000 | |
| EP | 620862 B1 | 4/1998 | |
| EP | 1138782 A2 | 10/2001 | |
| EP | 1234888 A2 | 8/2002 | |
| EP | 1333101 A1 | 8/2003 | |
| GB | 2325002 A | 11/1998 | |
| GB | 2339905 A | 2/2000 | |
| JP | 2004-201641 | * | 7/2004 |
| WO | WO9015157 A1 | 12/1990 | |
| WO | WO9208117 A1 | 5/1992 | |
| WO | WO9209703 A1 | 6/1992 | |
| WO | WO9303186 A1 | 2/1993 | |
| WO | WO9305182 A1 | 3/1993 | |
| WO | WO9308297 A1 | 4/1993 | |
| WO | WO9416101 A2 | 7/1994 | |
| WO | WO9421822 A1 | 9/1994 | |
| WO | WO9504161 A1 | 2/1995 | |
| WO | WO9513396 A2 | 5/1995 | |
| WO | WO9629431 A2 | 9/1996 | |
| WO | WO9632504 A2 | 10/1996 | |
| WO | WO9635450 A1 | 11/1996 | |
| WO | WO9637630 A1 | 11/1996 | |
| WO | WO9733000 A1 | 9/1997 | |
| WO | WO9737041 A2 | 10/1997 | |
| WO | WO9803684 A1 | 1/1998 | |
| WO | WO9812355 A1 | 3/1998 | |
| WO | WO9814616 A1 | 4/1998 | |
| WO | WO9815652 A1 | 4/1998 | |
| WO | WO9820020 A2 | 5/1998 | |
| WO | WO9820157 A2 | 5/1998 | |
| WO | WO9820166 A2 | 5/1998 | |
| WO | WO9826095 A1 | 6/1998 | |
| WO | WO9831830 A1 | 7/1998 | |
| WO | WO9840520 A1 | 9/1998 | |
| WO | WO9854751 A1 | 12/1998 | |
| WO | WO9905319 A2 | 2/1999 | |
| WO | WO9912040 A2 | 3/1999 | |
| WO | WO9929898 A2 | 6/1999 | |
| WO | WO9957318 A2 | 11/1999 | |
| WO | WO0107648 A1 | 2/2001 | |
| WO | WO0123604 A2 | 4/2001 | |
| WO | WO0132930 A1 | 5/2001 | |
| WO | WO0151661 A2 | 7/2001 | |
| WO | WO0157263 A1 | 8/2001 | |
| WO | WO0157518 A2 | 8/2001 | |
| WO | WO0173199 A1 | 10/2001 | |
| WO | WO0210186 A1 | 2/2002 | |
| WO | WO0210444 A1 | 2/2002 | |
| WO | WO0218641 A2 | 3/2002 | |
| WO | WO0221108 A2 | 3/2002 | |
| WO | WO0222873 A1 | 3/2002 | |
| WO | WO0250307 A1 | 6/2002 | |
| WO | WO02057491 A2 | 7/2002 | |
| WO | WO02070664 A2 | 9/2002 | |
| WO | WO02077278 A1 | 10/2002 | |
| WO | WO02099034 A2 | 12/2002 | |
| WO | WO03002750 A2 | 1/2003 | |
| WO | WO03008636 A2 | 1/2003 | |
| WO | WO03016546 A1 | 2/2003 | |
| WO | WO03060163 A2 | 7/2003 | |
| WO | WO03088979 A2 | 10/2003 | |
| WO | WO03093506 A2 | 11/2003 | |
| WO | WO03097869 A2 | 11/2003 | |
| WO | WO03102191 A1 | 12/2003 | |
| WO | WO2004013357 A2 | 2/2004 | |
| WO | WO2005024046 A2 | 3/2005 | |
| WO | WO2007086904 A2 | 8/2007 | |

OTHER PUBLICATIONS

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Barbour A.G., et al., "Identification of an Uncultivatable Borrelia Species in the Hard Tick Amblyomma Americanum: Possible Agent of a Lyme Disease-Like Illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Barr I.G., et al., "An Influenza A(H3) Reassortant was Epidemic in Australia and New Zealand in 2003," Journal of Medical Virology, 2005, vol. 76 (3), pp. 391-397.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Boivin-Jahns V., et al., "Bacterial Diversity in a Deep-Subsurface Clay Environment," Applied and Environmental Microbiology, 1996, vol. 62 (9), pp. 3405-3412.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Carracedo A., et al., "DNA Commission of the International Society for Forensic Genetics: Guidelines Formitochondrial DNA Typing," Forensic Science International, 2000, vol. 110 (2), pp. 79-85.
Case J.T., et al., "Maternal Inheritance of Mitochondrial DNA Polymorphisms in Cultured Human Fibroblasts," Somatic Cell Genetics, 1981, vol. 7 (1), pp. 103-108.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chen C.H., et al., Laser Desorption Mass Spectrometry for FastDNA Sequencing [online], Nov. 1994, Retrieved from the Internet:< URL:http://www.ornl.gove/sci/techresources/Human_Genome/publicat/94SANTA/sequencing/seqtoc.shtml>.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Co-pending U.S. Appl. No. 90/010,209, filed on Jun. 27, 2008.
Co-pending U.S. Appl. No. 90/010,210, filed on Jun. 27, 2008.
Crespillo M., et al., "Mitochondrial DNA Sequences for 118 Individuals from Northeastern Spain," International Journal of Legal Medicine, 2000, vol. 114 (1-2), pp. 130-132.
Database WPI Week 200454 Derwent Publications Ltd., London, GB; AN 2004-556368 XP002462655 & JP 2004 201641 A (Mitsubishi YUKA BCL KK) Jul. 22, 2004 abstract.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Ecker Supporting Information [online], May 23, 2005 [retrieved on Jul. 31, 2011]. Retrieved from the Internet:<URL: http://www.pnas.org/content/102/22/8012/suppl/DC1>.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.
EMBL "Human, muscle, Mitochondrial Mutant, 22 nt, segment 2 of 2," Accession No. S90302, Sep. 1, 2004.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.
Final Office Action mailed Oct. 14, 2009 for U.S. Appl. No. 10/943,344 filed Sep. 17, 2004.
Fraser C.M., et al., "The Mimimal Gene Complement of Mycoplasma Genitalium," Science, 1995, vol. 270 (5235), pp. 397-403.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Genbank, "Clostridium Tetani E88, Complete Genome," Accession No. AE015927.1, Feb. 4, 2003.
Genbank, "Enterococcus Malodoratus Strain ATCC43197 Elongation Factor Tu (tufA) Gene, Partial Cds," Accession No. AF274728, Dec. 11, 2000.
Genbank "Staphylococcus Aureus Strain MSSA476, Complete Genome," Accession No. BX571857.1, Jun. 24, 2004.
Genbank, "Staphylococcus Epidermidis ATCC 12228, Complete Genome," Accession No. AE015929.1, Jan. 2, 2003.
Genbank "Streptococcus Agalactiae 2603V/R, Complete Genome," Accession No. AE009948.1, Aug. 28, 2002.
Genbank, "Streptococcus Anginosus Elongation Factor Tu (tuf) Gene, Partial cds," Accession No. AF276257.1, Jul. 1, 2001.
Genbank, "Streptococcus Pyogenes Strain MGAS8232, Complete Genome," Accession No. AE009949.1, Apr. 3, 2002.
Gendel S.M., "Computational Analysis of the Specificity of 16S rRNA-Derived Signature Sequencesfor Identifying Food-Related Microbes," Food Microbiology, 1996, vol. 13, pp. 1-15.
Giles R.E., et al., "Maternal Inheritance of Human Mitochondrial DNA," Proceedings of the National Academy of Sciences, 1980, vol. 77 (11), pp. 6715-6719.
Ginther C., et al., "Identifying Individuals by Sequencing Mitochondrial DNA from Teeth," Nature Genetics, 1992, vol. 2 (2), pp. 135-138.
Goto K., et al., "Applications of the Partial 16S rDNA Sequence as an Index for Rapid Identification of Species in the Genus Bacillus," Journal of General and Applied Microbiology, 2000, vol. 46 (1), pp. 1-8.
Greenberg B.D., et al., "Intraspecific Nucleotide Sequence Variability Surrounding the Origin of Replicationin Human Mitochondrial DNA," Gene, 1983, vol. 21, pp. 33-49.
Griffin T.J., et al., "Single-Nucleotide Polymorphism Analysis by Maldi-TOF Mass Spectrometry," Trends in Biotechnology, 2000, vol. 18 (2), pp. 77-84.
Grzybowski T., et al., "Extremely High Levels of Human Mitochondrial DNA Heteroplasmy in Single Hair Roots," Electrophoresis, 2000, vol. 21 (3), pp. 548-553.
Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hofstadler S.A., et al., "TIGER: The Universal Biosensor," International Journal of Mass Spectrometry, 2005, vol. 242, pp. 23-41.

Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.

Holm L., et al., "Removing Near-Neighbour Redundancy from Large Protein Sequence Collections," Bioinformatics, 1998, vol. 14 (5), pp. 423-429.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hurst G.B., et al., "MALDI-TOF Analysis of Polymerase Chain Reaction Products from Methanotrophic Bacteria," Analytical Chemistry, 1998, vol. 70 (13), pp. 2693-2698.

Hutchison C.A., et al., "Maternal Inheritance of Mammalian Mitochondrial DNA," Nature, 1974, vol. 251 (5475), pp. 536-538.

Ingman M., et al., "Mitochondrial Genome Variation and the Origin of Modern Humans," Nature, 2000, vol. 408 (6813), pp. 708-713.

International Search Report for Application No. PCT/US2007/066194, mailed on Jan. 15, 2008, 4 pages.

International Search Report for Application No. PCT/US2009/045635, mailed on Oct. 7, 2009, 9 pages.

Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.

Jackson P.E., et al., "Mass Spectrometry for Genotyping: an Emerging Tool for Molecular Medicine," Molecular Medicine Today, 2000, vol. 6 (7), pp. 271-276.

James A.M., et al., "*Borelia lonestari* Infection after a Bite by an Amblyomma Americanum Tick," The Journal of Infectious Diseases, 2001, vol. 183 (12), pp. 1810-1814.

Jankowski K., et al., "Mass Spectrometry of DNA. Part 2 Quantitative Estimation of Base Composition," European Journal of Mass Spectrometry, 1980, vol. 1 (1), pp. 45-52.

Jansen R.C., et al., "Genotype-by-environment Interaction in Genetic Mapping of Multiple Quantitative Trait Loci," Theoretical and Applied Genetics, 1995, vol. 91, pp. 33-37.

Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.

Jiang C., et al., "Multiple Trait Analysis of Genetic Mapping for Quantitative Trait Loci Genetics," Genetics, 1995, vol. 140 (3), pp. 1111-1127.

Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.

Johansson A., et al., "Evaluation of PCR-based Methods for Discrimination of Francisella species and Subspecies and Development of a Specific PCR that Distinguishes the Two Major Subspecies of Francisella Tularensis," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.

Johnson Y.A., et al., "Precise Molecular Weight Determination of PCR Products of the rRNA Intergenic Spacer Region Using Electrospray Quadrupole Mass Spectrometry for Differentiation of B. Subtilis and B. Atrophaeus, Closely Related Species of *Bacilli*," Journal of Microbiological Methods, 2000, vol. 40 (3), pp. 241-254.

Jurinke C., et al., "Application of Nested PCR and Mass Specctrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.

Jurinke C., et al., "MALDI-TOF Mass Spectrometry. A Versatile Tool for High-Performance DNA Analysis," Molecular Biotechnology, 2004, vol. 26 (2), pp. 147-163.

Ke D., et al., "Development of a PCR Assay for Rapid Detection of Enterococci," Journal of Clinical Microbiology, 1999, vol. 37 (11), pp. 3497-3503.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Kilpatrick D.R., et al., "Group-Specific Identification of Polioviruses by PCR Using Primer Containing Mixed- Base or Deoxyinosine Residues at Positions of Codon Degeneracy," Journal of Clinical Microbiology, 1996, vol. 34 (12), pp. 2990-2996.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li J., et al., "Single Nucleotide Polymorphism Determination Using Primer Extension and Time-of-Flight Mass Spectrometry," Electrophoresis, 1999, vol. 20 (6), pp. 1258-1265.

Limbach P.A., et al., "Enzymatic Sequencing of Oligonucleotides with Electrospray Mass Spectrometry," 42nd ASMS Conference on Mass Spectrometry, 1994.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Liu C., et al., "Improving the Microdialysis Procedure for Electrospray Ionization Mass Spectrometry of Biological Samples," Journal of Mass Spectrometry, 1997, vol. 32 (4), pp. 425-431.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Matray T.J., et al., "Synthesis and Properties of RNA Analogs-Oligoribonucleotide N3—>p5 Phosphoramidates," Nucleic Acids Research, 1999, vol. 27 (20), pp. 3976-3985.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Miller K.W., et al., "A Compendium of Human Mitochondrial DNA Control Region: Development of an International Standard Forensic Database," Croatian Medical Journal, 2001, vol. 42 (3), pp. 315-327.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Nakao H., et al., "Development of a Direct PCR Assay for Detection of the Diphtheria Toxin Gene," Journal of Clinical Microbiology, 1997, vol. 35 (7), pp. 1651-1655.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ng E.K., et al., "Serial Analysis of the Plasma Concentration of SARS Coronavirus RNA In Pediatric Patients with Severe Acute Respiratory Syndrome," Clinical Chemistry, 2003, vol. 49 (12), pp. 2085-2088.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstitution of Active Recombinant Ship Toxin (Stc)1 from Recombinant Stx1 -A and Sbt1 -B Subunits Independently Produced by E. Coli Clones," FEMS Microbiol Letters, 1999, vol. 178 (1), pp. 13-18.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.

Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.

Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.

Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.

Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Office Action mailed May 4, 2010 for U.S. Appl. No. 90/010,447, filed Apr. 9, 2009.

Office Action mailed May 4, 2010 for U.S. Appl. No. 90/010,448, filed Apr. 9, 2009.

Office Action mailed Apr. 7, 2009 for European Application No. 07760292.8 filed Apr. 6, 2007.

Office Action mailed Dec. 7, 2010 for European Application No. 07760292.8 filed Apr. 6, 2007.

Office Action mailed Dec. 9, 2009 for U.S. Appl. No. 90/010,210, filed Jun. 27, 2008.

Office Action mailed Dec. 9, 2009 for U.S. Appl. No. 90/010,447, filed Apr. 9, 2009.

Office Action mailed Dec. 9, 2009 for U.S. Appl. No. 90/010,448, filed Apr. 9, 2009.

Office Action mailed Jun. 10, 2009 for U.S. Appl. No. 90/010,210, filed Jun. 27, 2008.

Office Action mailed Jun. 10, 2010 for U.S. Appl. No. 90/010,447, filed Apr. 9, 2009.

Office Action mailed Jun. 10, 2010 for U.S. Appl. No. 90/010,448, filed Apr. 9, 2009.

Office Action mailed Aug. 11, 2010 for U.S. Appl. No. 90/010,447, filed Apr. 9, 2009.

Office Action mailed Aug. 11, 2010 for U.S. Appl. No. 90/010,448, filed Apr. 9, 2009.

Office Action mailed Jun. 11, 2010 for U.S. Appl. No. 90/010,210, filed Jun. 27, 2008.

Office Action mailed Apr. 16, 2009 for U.S. Appl. No. 90/010,210, filed Jun. 27, 2008.

Office Action mailed Sep. 20, 2010 for U.S. Appl. No. 90/010,447, filed Apr. 9, 2009.

Office Action mailed Sep. 20, 2010 for U.S. Appl. No. 90/010,448, filed Apr. 9, 2009.

Office Action mailed Apr. 21, 2009 for U.S. Appl. No. 90/010,209, filed Jun. 27, 2008.

Office Action mailed Jul. 22, 2008 for U.S. Appl. No. 90/010,209, filed Jun. 27, 2008.

Office Action mailed Jul. 22, 2008 for U.S. Appl. No. 90/010,210, filed Jun. 27, 2008.

Office Action mailed Apr. 23, 2010 for U.S. Appl. No. 90/010,210, filed Jun. 27, 2008.

Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Jun. 25, 2009 for U.S. Appl. No. 90/010,210, filed Jun. 27, 2008.
Office Action mailed Jul. 28, 2010 for U.S. Appl. No. 90/010,210, filed Jun. 27, 2008.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Olsen B., et al., "Transhemispheric Exchange of Lyme Disease Spyrochetes by Seabirds," Journal of Clinical Microbiology, 1995, vol. 33 (12), pp. 3270-3274.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pieles U., et al., "Matrix-Assisted Laser Desorption Ionization Time-of-Flight Spectrometry: A Powerful Tool for the Mass and Sequence Analysis of Natural and Modified Oligonucleotides," Nucleic Acids Research, 1993, vol. 21 (14), pp. 3191-3196.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Schena M., et al., "Genome Analysis with Gene Expression Microarrays," Bioessays, 1996, vol. 18 (5), pp. 427-431.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Sciacchitano C.J., "Analysis of Polymerase Chain Reaction-Amplified DNA Fragments of Clostridium Botulinum Type E Neurotoxin Gene By High Performance Capillary Electrophoresis," Journal of Liquid Chromatography & Related Technologies, 1996, vol. 19 (13), pp. 2165-2178.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Sumner J.W., et al., "PCR Amplification and Comparison of Nucleotide Sequences from the groESL Heat Shock Operon of Ehrlichia Species," Journal of Critical Microbiology, 1997, vol. 35 (8), pp. 2087-2092.
Supplementary European Search Report for Application No. EP05753037, mailed on Aug. 21, 2009, 2 pages.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Torroni A., et al., "Classification of European mtDNAs from an Analysis of Three European Populations," Genetics, 1996, vol. 144 (4), pp. 1835-1850.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.
Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.
Unal S., et al., "Detection of Methicillin-Resistant Staphylococci by Using the Polymerase Chain Reaction," Journal of Clinical Microbiology, 1992, vol. 30 (7), pp. 1685-1691.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Ert M.N., et al., "Mass Spectrometry Provides Accurate Characterization of Two Genetic Marker Types in *Bacillus anthracis*," Bio Techniques, 2004, vol. 37 (4), pp. 642-651.
Vanderhallen H., et al., "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.

Welham K.J., et al., "The Characterization of Micro-Organisms by Matrix-Assisted Laser Desorption/Ionization Time-of-Flight Mass Spectrometry," Rapid Communications in Mass Spectrometry, 1998, vol. 12 (4), pp. 176-180.

Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.

Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.

Xu L., et al., "Electrophore Mass Tag Dideoxy DNA Sequencing," Analytical Chemistry, 1997, vol. 69 (17), pp. 3595-3602.

Yao Z.P., et al., "Mass Spectrometry Based Proteolytic Mapping for Rapid Virus Identification," Analytical Chemistry, 2002, vol. 74 (11), pp. 2529-2534.

Zeng Z.B., "Precision Mapping of Quantitative Trait Loci," Genetics, 1994, vol. 136 (4), pp. 1457-1468.

* cited by examiner

SEQUENCE LISTING

<160> NUMBER OF SEQ ID NOS: 32

<210> SEQ ID NO 1
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgaggtctg ggtaatcttg tgaaact                                        27

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgataacga acgagacctt aacc                                           24

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgctgcgata acgaacgaga ccttaa                                         26

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcccgggtga ttcataataa cttctcg                                        27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgtagaata agtgggagct tcggc                                          25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tctcaggata gcagaaactc gtatcag                                        27

<210> SEQ ID NO 7
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
tccgtctaac atctatgcga gtgttt                                              26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgaagcgg caaaagctca aatttg                                              26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctcaggata gcagaagctc gtatcag                                             27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgtgaagcgg caaaagctca aattt                                               25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggagtctaa catctatgcg agtgtt                                              26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgtagaata ggtgggagct tcggc                                               25

<210> SEQ ID NO 13

<400> SEQUENCE: 13

000
```

<210> SEQ ID NO 14

<400> SEQUENCE: 14

000

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgcgaggtat tcctcgttga agagc                                          25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcctgttatt gcctcaaact tccatc                                         26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcacagacct gttattgcct caaact                                         26

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgcgaccatg gtaggcctct atc                                            23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttccccacct gacaatgtct tcaac                                          25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
tcgcccacgt ccaattaagt aacaa                                          25

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcagctatgc tcttactcaa atccatcc                                       28

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcacgggatt ctcaccctct gtg                                            23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcaccctcta tgacgcccta ttcc                                           24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccacgttca attaagcaac aaggac                                         26

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttctcaccct ctgtgacggc ctgttcc                                        27

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```

```
tcagctatgc tcttactcaa atccatc                                        27
```

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
tgacaatgtc ttcaacccgg atc                                            23
```

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: Propynylated T
<220> FEATURE:
<221> NAME/KEY: modified_base
<222> LOCATION: (22)..(22)
<223> OTHER INFORMATION: Propynylated C

<400> SEQUENCE: 28

```
ttgtagaata agtgggagct tcggc                                          25
```

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: Propynylated C
<220> FEATURE:
<221> NAME/KEY: modified_base
<222> LOCATION: (18)..(18)
<223> OTHER INFORMATION: Propynylated T
<220> FEATURE:
<221> NAME/KEY: modified_base
<222> LOCATION: (19)..(19)
<223> OTHER INFORMATION: Propynylated C
<220> FEATURE:
<221> NAME/KEY: modified_base
<222> LOCATION: (23)..(24)
<223> OTHER INFORMATION: Propynylated T

<400> SEQUENCE: 29

```
tgtgaagcgg caaaagctca aatttg                                         26
```

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: Propynylated T
<220> FEATURE:
<221> NAME/KEY: modified_base -continued

```
<222> LOCATION: (22)..(22)
<223> OTHER INFORMATION: Propynylated C

<400> SEQUENCE: 30
ttccccacct gacaatgtct tcaac                                          25

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(17)
<223> OTHER INFORMATION: Propynylated C

<400> SEQUENCE: 31
tcacgggatt ctcaccctct gtg                                            23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (4)..(6)
<223> OTHER INFORMATION: Propynylated C
<220> FEATURE:
<221> NAME/KEY: modified_base
<222> LOCATION: (21)..(22)
<223> OTHER INFORMATION: Propynylated T

<400> SEQUENCE: 32
tcaccctcta tgacgcccta ttcc                                           24
```

COMPOSITIONS FOR THE USE IN IDENTIFICATION OF FUNGI

CROSS REFERENCE TO RELATED APPLICATIONS

This application is a 371 national stage entry of PCT International Patent Application No. PCT/US2007/066194, filed Apr. 6, 2007, which claims priority to expired U.S. Provisional Application No. 60/790,499 filed Apr. 6, 2006, each of which are herein incorporated by reference in their entireties.

STATEMENT REGARDING FEDERALLY SPONSORED RESEARCH OR DEVELOPMENT

This invention was made with government support under contract RO1 CI000099-01 awarded by the Centers for Disease Control. The government has certain rights in the invention.

FIELD

Provided herein are compositions, kits and methods for rapid identification and quantification of fungi by molecular mass and base composition analysis.

BACKGROUND

The diagnosis of invasive fungal infections (IFI) is a major unmet medical need. As many as 15% of patients with allogeneic hematopoietic stem cell transplant develop IFI, mostly caused by *Aspergillus*. Patients with prolonged neutropenia (due to any cause) or immunosuppression (due to transplants or treatment with corticosteroids) are at particularly high risk.

Currently, the diagnosis of IFI relies on a combination of clinical and laboratory criteria. The criteria were developed as an international consensus and the certainty of the diagnosis ranges from definite (detection of the fungus in tissue) to probable or possible. Because definite diagnosis requires biopsy and visualization of the organism in tissue, the majority of patients with IFI fall into the probable or possible categories. Even when a histologic diagnosis is made, the mold cannot be definitively identified because molds grow as hyphae in tissue and do not form spores. Since the anti-fungal susceptibility of different genera and species differs, specific diagnosis is of great clinical importance. There are now effective and relatively non-toxic therapies available for IFI, especially those caused by *Aspergillus fumigatus*. Thus, the diagnostic limitations have profound effects on the treatment of IFI.

It is challenging to diagnose IFI non-invasively, as it is difficult to successfully culture fungi from blood or respiratory secretions. Complicating the problem, fungi are common in the environment and, thus, a positive culture could be due to environmental contamination. Two non-invasive assays are available. An assay for circulating galactomannan, a constituent of the *Aspergillus* cell wall, has recently been approved by the FDA. As fungi other than *Aspergillus* do not have galactomannan in their cell walls, a negative test does not exclude IFI. Furthermore, the sensitivity and specificity of the galactomannan assay vary greatly from study to study for reasons that include technical differences in how the test is performed in the U.S. and Europe, the incidence of aspergillosis in the population tested, and low sample size. A test is also available for circulating glucan, a component of all fungal cell walls. This test should be of wider utility than that for galactomannan, although it has not been as widely studied as the galactomannan assay.

Invasive candidiasis can occur in severely immunosuppressed individuals and in patients who have central venous catheters, especially if they are on systemic antibiotics and/or parenteral nutrition. The diagnosis of invasive candidiasis currently rests primarily on detection of the organism in blood cultures. In the correct clinical setting, positive cultures from respiratory secretions and urine raise the suspicion of systemic infection. The diagnosis of the species of *Candida* is important because *Candida albicans* is much more susceptible to fluconazole than other species of *Candida*, especially *C. krusei*. Species identification of the organism can take up to 10 or more days, although the presence of *Candida* can be determined fairly quickly (1-2 days).

There have been many attempts to develop a diagnostic test for fungal DNA. Blood and bronchoalveolar lavage fluid have been the main fluids studied. Although different DNA extraction methods, various target genes and primers, and a variety detection methods and analytical techniques have been used, none of the published techniques have shown a strong enough correlation with clinical diagnosis to establish any as a preferred approach.

SUMMARY

Provided herein are compositions, kits and methods for rapid identification and quantification of fungi by molecular mass and base composition analysis.

One embodiment provides an isolated oligonucleotide primer pair having a forward primer member and a reverse primer member. Preferably, the forward primer member and the reverse primer member are independently 13-35 nucleobases in length and are configured to hybridize with a target nucleic acid to generate an amplicon that is from about 45 to about 200 nucleobases in length. In this preferred embodiment the target nucleic acid is a fungi reference sequence. Fungi reference sequences include, GenBank Accession No.: X53497.1 (gi No.: 2507); and GenBank Accession No.: X70659 (gi No.: 671812). In this preferred embodiment the forward and reverse primer members are individually configured to have 70% or greater complementarity to the target sequence.

The isolated oligonucleotide primer pair are configured to generate an amplicon from a plurality of fungi bioagents, wherein at least two of the generated amplicons will have unique molecular masses when analyzed suing mass spectrometry. The unique molecular masses identify individual fungi bioagents from the plurality of fungi bioagents. Identification is achieved by comparing the unique molecular masses to a database of molecular masses that are indexed to known fungi bioagents and to the primer pairs used to generate the amplicon. Alternatively, base compositions can be calculated from the molecular masses and the base compositions are queried to a database comprising base compositions indexed to fungi bioagents and to the primer pairs used to generate the amplicons.

Thus, in a further embodiment there is provided a method for the identification of fungi bioagents using the isolated oligonucleotide primer pairs. In the preferred embodiment of the method, at least one isolated oligonucleotide primer pair is used to amplify nucleic acid from a sample. The sample is suspected of comprising nucleic acid from one or more fungi bioagents. Each amplicon is analyzed using mass spectrometry to determine the molecular mass of said amplicon. Alternatively, base compositions are calculated from the molecular masses determined for the amplicons. The molecular mass and/or the base composition is then queried against a database of molecular masses and/or base compositions. A match between the experimental data and the database data identifies In one embodiment there is provided a database comprising molecular mass and/or base composition data. In this embodiment, the molecular mass and/or base composition data is indexed to fungi bioagents and oligonucleotide primer pairs. The database data represents the molecular mass and/or base composition results that are achieved by using a particular primer pair on a particular known fungi bioagent. Thus, by indexing the molecular mass and/or base composition data with a primer pair and a known bioagent, the query scans the experimentally derived molecular mass or base composition data through a plurality of molecular mass or base composition database data for each of the corresponding oligonucleotide primer pairs until a match is found. The match identifies the bioagent in the sample. In a preferred embodiment the database comprises base composition data.

In one embodiment there is a method for the identification of a fungi bioagent in a sample comprising the step of experimentally generating a molecular mass or a base composition and comparing that molecular mass or base composition to a molecular mass or base composition from at least one known fungal bioagent wherein a match identifies the fungi bioagent in said sample.

One embodiment is an oligonucleotide primer 14 to 35 nucleobases in length having at least 70% sequence identity with SEQ ID NO: 12.

Another embodiment is an oligonucleotide primer 14 to 35 nucleobases in length having at least 70% sequence identity with SEQ ID NO: 27.

Another embodiment is a composition of is an isolated oligonucleotide primer pair including a forward primer member 14 to 35 nucleobases in length having at least 70% sequence identity with SEQ ID NO: 12 and a reverse primer member 14 to 35 nucleobases in length having at least 70% sequence identity with SEQ ID NO: 27.

One embodiment is an oligonucleotide primer 14 to 35 nucleobases in length having at least 70% sequence identity with SEQ ID NO: 9.

Another embodiment is an oligonucleotide primer 14 to 35 nucleobases in length having at least 70% sequence identity with SEQ ID NO: 24.

Another embodiment is a composition of is an oligonucleotide primer pair including an oligonucleotide primer 14 to 35 nucleobases in length having at least 70% sequence identity with SEQ ID NO: 9 and an oligonucleotide primer 14 to 35 nucleobases in length having at least 70% sequence identity with SEQ ID NO: 24.

One embodiment is an oligonucleotide primer 14 to 35 nucleobases in length having at least 70% sequence identity with SEQ ID NO: 10.

Another embodiment is an oligonucleotide primer 14 to 35 nucleobases in length having at least 70% sequence identity with SEQ ID NO: 25.

Another embodiment is a composition of is an oligonucleotide primer pair including an oligonucleotide primer 14 to 35 nucleobases in length having at least 70% sequence identity with SEQ ID NO: 10 and an oligonucleotide primer 14 to 35 nucleobases in length having at least 70% sequence identity with SEQ ID NO: 25.

One embodiment is an oligonucleotide primer 14 to 35 nucleobases in length having at least 70% sequence identity with SEQ ID NO: 11.

Another embodiment is an oligonucleotide primer 14 to 35 nucleobases in length having at least 70% sequence identity with SEQ ID NO: 26.

Another embodiment is a composition of is an oligonucleotide primer pair including an oligonucleotide primer 14 to 35 nucleobases in length having at least 70% sequence identity with SEQ ID NO: 11 and an oligonucleotide primer 14 to 35 nucleobases in length having at least 70% sequence identity with SEQ ID NO: 26.

In some embodiments, either or both of the primer members of the primer pair contain at least one modified nucleobase such as 5-propynyluracil or 5-propynylcytosine for example.

In some embodiments, either or both of the primer members of the primer pair comprises at least one universal nucleobase such as inosine for example.

In some embodiments, either or both of the primer members of the primer pair comprises at least one non-templated T residue on the 5'-end.

In some embodiments, either or both of the primer members of the primer pair comprises at least one non-template tag.

In some embodiments, either or both of the primer members of the primer pair comprises at least one molecular mass modifying tag.

In some embodiments, either or both of the primer members of the primer pair comprises at least one non-templated T nucleotide at the 5' end of said primer member.

Some embodiments are kits that contain the isolated oligonucleotides primer pair compositions. In some embodiments, each member of said one or more isolated oligonucleotides primer pairs of the kit is independently of a length of 14 to 35 nucleobases and has 70% to 100% sequence identity with the corresponding member from the group of primer pairs represented by SEQ ID NO: 9: SEQ ID NO: 24; SEQ ID NO: 10: SEQ ID NO: 25; SEQ ID NO: 11: SEQ ID NO: 26; and SEQ ID NO: 12: SEQ ID NO: 27.

Some embodiments of the kits contain at least one calibration polynucleotide.

Some embodiments of the kits contain at least one anion exchange functional group linked to a magnetic bead.

In some embodiments, there is provided primers and compositions comprising isolated pairs of oligonucleotides primers, and kits containing the same, and methods for use in identification of fungi. The primers are configured to produce amplification products of DNA encoding genes that have conserved and variable regions among fungi. Further provided are compositions comprising isolated pairs of oligonucleotides primers and kits containing the same, which are configured to provide species and sub-species characterization of fungi.

Some embodiments provide methods for determining the quantity of an unknown fungus in a sample. The sample is contacted with the composition described above and a known quantity of a calibration polynucleotide comprising a calibration sequence. Nucleic acid from the unknown fungus in the sample is concurrently amplified with the composition described above and nucleic acid from the calibration polynucleotide in the sample is concurrently amplified with the composition described above to obtain a first amplification product comprising a fungal identifying amplicon and a second amplification product comprising a calibration amplicon. The molecular mass and abundance for the fungal identifying amplicon and the calibration amplicon is determined. The fungal identifying amplicon is distinguished from the calibration amplicon based on molecular mass, wherein comparison of fungal identifying amplicon abundance and calibration amplicon abundance indicates the quantity of fungus in the sample. In some embodiments, the base composition of the fungal identifying amplicon is determined.

In some embodiments, there are methods for detecting or quantifying fungi by combining a nucleic acid amplification process with a mass determination process. In some embodiments, such methods identify or otherwise analyze the fungi by comparing mass information from an amplification product with a calibration or control product. Such methods can be carried out in a highly multiplexed and/or parallel manner allowing for the analysis of as many as 300 samples per 24 hours on a single mass measurement platform. The accuracy of the mass determination methods in some embodiments permits allows for the ability to discriminate between different fungi such as, for example, pathogenic fungi which are members of the phyla Zygomycota, Basidomycota, Ascomycota, and Fungi incertae sedis. Pathogenic classes within the phylum Zygomycota include zygomycetes of which member species include, but are not necessarily limited to: *Absidia corymbifera*, *Mucor circinelloides*, *Mucor hiemalis*, *Rhizopus oryzae*, and *Rhizopus microsporus*. Pathogenic classes within the phylum Basidomycota include, but are not necessarily limited to Ustilaginomycetes which includes the species *Malassezia furfur*, and Hymenomycetes which includes the member species *Cryptococcus neoformans*, *Trichosporon cutaneum*, *Trichosporon*, *asahii*, and *Trichosporon capitatum*. Pathogenic classes within the phylum Ascomycota include but are not necessarily limited to: Saccharomycetes which includes the species *Clavispora lusitaniae*, *Candida albicans*, *Candida dubliniensis*, *Candida glabrata*, *Candida krusei*, *Candida parapsilosis* and *Candida tropicalis*, Eurotiales which includes the species *Aspergillus flavus*, *Aspergillus fumigatus*, *Aspergillus niger*, *Aspergillus terreus*, and *Aspergillus oryzae*, Ophiostomatales which includes the species *Sporothrix schenckii*, Onygenales which includes the species *Microsporum audouini*, *Microsporum canis*, *Microsporum gypseum*, *Trichophyton mentagrophytes*, *Trichophyton rubrum*, *Trichophyton tonsurans*, *Trichophyton violaceum*, *Ajellomyces dermatitidis*, *Coccidioides immitis*, *Epidermophyton floccosum*, *Histoplasma capsulatum*, and *Paracoccidioides brasiliensis*, Ascomycota incertae sedis which includes the species *Cladosporium werneckii*, and Anamorphic Ascomycota which includes the species *Penicillium marneffei*, *Fusarium oxysporum*, *Fusarium solani*, *Hortaea wemecki*, *Paecilomyces lilacinus*, *Paecilomyces variotii*, *scedosporium prolificans*, *scedosporium apiospermum*, and *Madurella grisea*. Pathogenic classes within the phylum Fungi incertae sedis include, but are not necessarily limited to, Pneumocystidales, which includes the species *Pneumocystis carinii*.

BRIEF DESCRIPTION OF THE DRAWINGS

The foregoing summary, as well as the following detailed description, is better understood when read in conjunction with the accompanying drawings which are included by way of example and not by way of limitation.

DEFINITIONS

Figure 1:
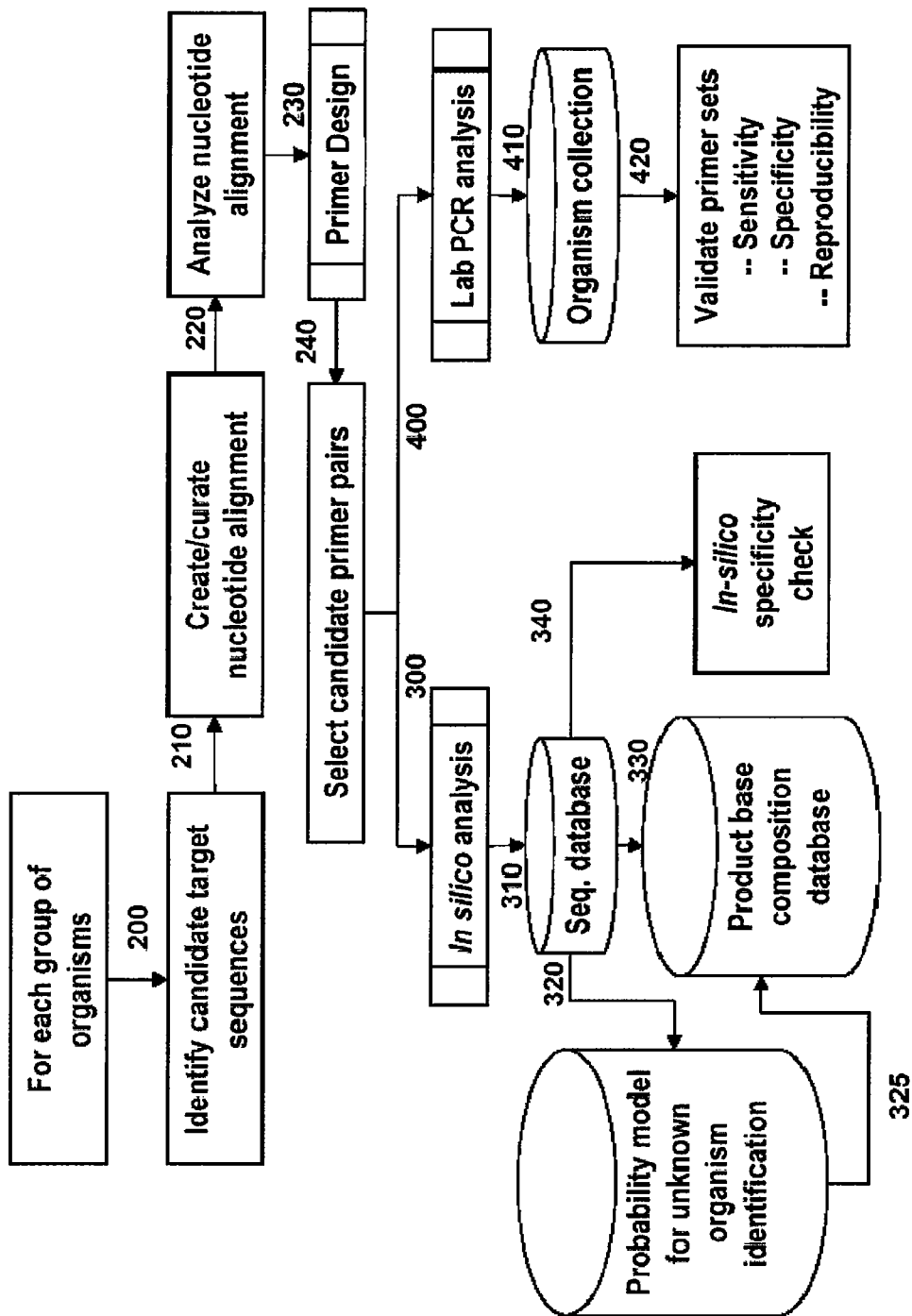
FIG. 1: process diagram illustrating a representative primer pair selection process.

As used herein, the term "abundance" refers to an amount. The amount may be described in terms of concentration which are common in molecular biology such as "copy number," "pfu or plate-forming unit" which are well known to those with ordinary skill. Concentration may be relative to a known standard or may be absolute.

As used herein, the term "amplifiable nucleic acid" is used in reference to nucleic acids that may be amplified by any amplification method. It is contemplated that "amplifiable nucleic acid" also comprises "sample template."

As used herein the term "amplification" refers to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been configured primarily for this sorting out. Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q.beta. replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplification reagents" refers to those reagents (deoxyribonucleotide triphosphates, buffer, etc.), needed for amplification, excluding primers, nucleic acid template, and the amplification enzyme. Typically, amplification reagents along with other reaction components are placed and contained in a reaction vessel (test tube, microwell, etc.).

As used herein, the term "anion exchange functional group" refers to a positively charged functional group capable of binding an anion through an electrostatic interaction. The most well known anion exchange functional groups are the amines, including primary, secondary, tertiary and quaternary amines.

As used herein, a "base composition" is the number of each nucleobase (for example, A, T, C and G) and nucleobase analogs. For example, amplification of nucleic acid of *Neis-*

*seria meningitidis* with a primer pair that produces an amplification product from nucleic acid of 23S rRNA that has a molecular mass (sense strand) of 28480.75124, from which a base composition of A25 G27 C22 T 18 is assigned from a list of possible base compositions calculated from the molecular mass using standard known molecular masses of each of the four nucleobases. Similarly, the same amplification product generated using nucleotide analogs (for example 5-iodo-C) has a base composition of A25 G27 5-iodo-C22 T18.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

As used herein, a "bioagent" is any organism, cell, or virus, living or dead, or a nucleic acid derived from such an organism, cell or virus. Examples of bioagents include, but are not limited, to cells, (including but not limited to human clinical samples, bacterial cells and other pathogens), viruses, fungi, protists, and parasites. Samples may be alive or dead or in a vegetative state (for example, vegetative bacteria or spores) and may be encapsulated or bioengineered. As used herein, a "pathogen" is a bioagent which causes a disease or disorder.

As used herein, a "bioagent division" is defined as group of bioagents above the species level and includes but is not limited to, orders, families, classes, clades, genera or other such groupings of bioagents above the species level.

As used herein, the term "bioagent identifying amplicon" refers to a polynucleotide that is amplified from a bioagent in an amplification reaction and which 1) provides sufficient variability to distinguish bioagents from one another to a significant level and 2) whose molecular mass is amenable to molecular mass determination methods such as mass spectrometry for example.

As used herein, the term "biological product" refers to any product originating from an organism. Biological products are often products of processes of biotechnology. Examples of biological products include, but are not limited to: cultured cell lines, cellular components, antibodies, proteins and other cell-derived biomolecules, growth media, growth harvest fluids, natural products and bio-pharmaceutical products.

The terms "biowarfare agent" and "bioweapon" are synonymous and refer to a bacterium, virus, fungus or protozoan that could be deployed as a weapon to cause bodily harm to individuals by military or terrorist groups.

The term "broad range survey primer pair" refers to a primer pair configured to produce bioagent identifying amplicons across different broad groupings of bioagents. For example, the ribosomal RNA-targeted primer pairs are broad range survey primer pairs.

The term "calibration amplicon" refers to a nucleic acid segment representing an amplification product obtained by amplification of a calibration sequence with a pair of primers configured to produce a bioagent identifying amplicon.

The term "calibration sequence" refers to a polynucleotide sequence to which a given pair of primers hybridizes for the purpose of producing an internal (i.e: included in the reaction) calibration standard amplification product for use in determining the quantity of a bioagent in a sample. The calibration sequence may be expressly added to an amplification reaction, or may already be present in the sample prior to analysis.

The term "clade primer pair" refers to a primer pair configured to produce bioagent identifying amplicons for species belonging to a clade group. A clade primer pair may also be considered as a speciating primer pair since it will have the capability of resolving species within the clade group.

The term "codon" refers to a set of three adjoined nucleotides (triplet) that codes for an amino acid or a termination signal.

As used herein, the term "codon base composition analysis," refers to determination of the base composition of an individual codon by obtaining a bioagent identifying amplicon that includes the codon. The bioagent identifying amplicon will at least include regions of the target nucleic acid sequence to which the primers hybridize for generation of the bioagent identifying amplicon as well as the codon being analyzed, located between the two primer hybridization regions.

As used herein, the terms "complementary" or "complementarity" are used in reference to polynucleotides (i.e., a sequence of nucleotides such as an oligonucleotide or a target nucleic acid) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The primer members of an oligonucleotides primer pair are complementary to the target nucleic acid. The primer members individually have 70% or greater complementarity to a target. The primer members are configured to hybridize with a plurality of fungi bioagents including, but not limited to, the reference bioagent. Thus, the complementarity of a primer member to the reference target or to any sample target to which it hybridizes is preferably 70% or greater. 70% or greater means all whole numbers from 70-100, as well as any fractions. So, for example, if a forward primer member is 22 nucleobases long and has 17 complementary nucleobases to the a target, and a reverse primer member is 25 nucleobases and has 20 complementary nucleobases to the target then the forward primer member is 77.3% complementary to the target and the reverse primer member is 80% complementary to the target. As used herein, 77.3% is rounded to 77%, while 77.5% would have rounded to 78%. Those of ordinary skill in the art understand primer complementarity. Primer members having less than 100% complementarity to a target comprise nucleotide insertions, deletions and additions compared to a 100% complementary primer member. 70% to 100% include the following whole numbers: 70% 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%.

The term "complement of a nucleic acid sequence" as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Where a first oligonucleotide is complementary to a region of a target nucleic acid and a second oligonucleotide has complementary to the same region (or a portion of this region) a "region of overlap" exists along the target nucleic acid. The degree of overlap will vary depending upon the extent of the complementarity As used herein, the term "division-wide primer pair" refers to a primer pair configured to produce bioagent identifying amplicons within sections of a broad spectrum of bioagents. For example, a primer pair configured to produce bioagent identifying amplicons for the beta-proteobacteria division of bacteria.

As used herein, the term "concurrently amplifying" used with respect to more than one amplification reaction refers to the act of simultaneously amplifying more than one nucleic acid in a single reaction mixture.

As used herein, the term "drill down primer pair" refers to a primer pair configured to produce bioagent identifying amplicons for identification of sub-species characteristics.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

As used herein, the term "etiology" refers to the causes or origins, of diseases or abnormal physiological conditions.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues ($^{18}/_{20}$=0.9 or 90% sequence identity). In another example, a primer 15 nucleobases in length having all residues identical to a 15 nucleobase segment of a primer 20 nucleobases in length would have $^{15}/_{20}$=0.75 or 75% sequence identity with the 20 nucleobase primer. Percentages can be whole numbers of fractions, as described above. Sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated Plus/Plus. Sequence identity may also encompass alternate or modified nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" refers to a gene encoding a protein or RNA involved in basic functions required for survival and reproduction of a bioagent. Housekeeping genes include, but are not limited to genes encoding RNA or proteins involved in translation, replication, recombination and repair, transcription, nucleotide metabolism, amino acid metabolism, lipid metabolism, energy generation, uptake, secretion and the like.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The term "isolated oligonucleotide primer pair," "isolated primer pair," "isolated primer," "isolated primer pair member" or "isolated oligonucleotide" refer to nucleic acid sequences that are substantially purified from components not of interest. Preferably, each of the primer members of the oligonucleotide primer pair are chemically synthesized and isolated using well-known techniques. Preferably, the isolated oligonucleotide primer pairs are and are at least 60% free from said components not of interest. Those of ordinary skill understand that at least 60% means 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% free from said components not of interest. In the most preferred embodiment each primer member is chemically synthesized and then either lyophilized or resuspended in an appropriate solution, such as Tris, EDTA (TE) buffer or HPLC water. Thus, an isolated oligonucleotide primer pair or an isolated primer pair member is purified from components not of interest.

The term "in silico" refers to processes taking place via computer calculations. For example, electronic PCR (ePCR) is a process analogous to ordinary PCR except that it is carried out using nucleic acid sequences and primer pair sequences stored on a computer formatted medium.

As described herein, oligonucleotides primers are configured to bind to conserved sequence regions of a plurality of bioagent that flank an intervening variable region and, upon amplification, yield amplification products which ideally provide enough variability to distinguish individual bioagents in said plurality, and which are amenable to molecular mass analysis. Preferably the conserved regions are highly conserved. By the term "highly conserved," it is meant that the sequence regions exhibit between about 80-100%, or between about 90-100%, or between about 95-100% identity among all, or at least 70%, at least 80%, at least 90%, at least 95%, or at least 99% of species or strains.

The "ligase chain reaction" (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. However, because the four oligonucleotides used in this assay can pair to form two short ligatable fragments, there is the potential for the generation of target-independent background signal. The use of LCR for mutant screening is limited to the examination of specific nucleic acid positions.

The term "locked nucleic acid" or "LNA" refers to a nucleic acid analogue containing one or more 2'-O, 4'-C-methylene-.beta.-D-ribofuranosyl nucleotide monomers in an RNA mimicking sugar conformation. LNA oligonucleotides display unprecedented hybridization affinity toward complementary single-stranded RNA and complementary single- or double-stranded DNA. LNA oligonucleotides induce A-type (RNA-like) duplex conformations.

As used herein, the term "mass-modifying tag" refers to any modification to a given nucleotide which results in an increase in mass relative to the analogous non-mass modified nucleotide. Mass-modifying tags can include heavy isotopes of one or more elements included in the nucleotide such as carbon-13 for example. Other possible modifications include addition of substituents such as iodine or bromine at the 5 position of the nucleobase for example.

The term "mass spectrometry" refers to measurement of the mass of atoms or molecules. The molecules are first converted to ions, which are separated using electric or magnetic fields according to the ratio of their mass to electric charge. The measured masses are used to identity the molecules.

The term "microorganism" as used herein means an organism too small to be observed with the unaided eye and includes, but is not limited to bacteria, virus, protozoans, fungi; and ciliates.

The term "multi-drug resistant" or multiple-drug resistant" refers to a microorganism which is resistant to more than one of the antibiotics or antimicrobial agents used in the treatment of said microorganism.

The term "multiplex PCR" refers to a PCR reaction where more than one primer set is included in the reaction pool allowing 2 or more different DNA targets to be amplified by PCR in a single reaction tube.

The term "non-templated T" refers to a nucleotide residue that is added to the 5' end of a primer pair member. The non-templated T residue is not complementary to the target nucleic acid sequence. The addition of a non-templated T residue has an effect of minimizing the addition of non-templated adenosine residues as a result of the non-specific enzyme activity of Taq polymerase (Magnuson et al., Biotechniques, 1996, 21, 700-709). Taq polymerase's non-specific enzyme activity will lead to ambiguous results during molecular mass analysis.

The term "non-template tag" refers to a stretch of at least three guanine or cytosine nucleobases of a primer used to produce a bioagent identifying amplicon which are not complementary to the template. A non-template tag is incorporated into a primer for the purpose of increasing the primer-duplex stability of later cycles of amplification by incorporation of extra G-C pairs which each have one additional hydrogen bond relative to an A-T pair.

The term "nucleic acid sequence" as used herein refers to the linear composition of the nucleic acid residues A, T, C or G or any analogs or modifications thereof, within an oligonucleotide, nucleotide or polynucleotide, and fragments or portions thereof, and to DNA or RNA of genomic or synthetic origin which may be single or double stranded, and represent the sense or antisense strand As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

The term "nucleotide analog" as used herein refers to modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

The term "oligonucleotide" as used herein is defined as a molecule comprising two or more deoxyribonucleotides or ribonucleotides, preferably at least 5 nucleotides, more preferably at least about 13 to 35 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5'-end" if its 5' phosphate is not linked to the 3' oxygen of a mononucleotide pentose ring and as the "3'-end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. All oligonucleotide primers disclosed herein are understood to be presented in the 5' to 3' direction when reading left to right. When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

As used herein, a "pathogen" is a bioagent which causes a disease or disorder.

As used herein, the terms "PCR product," "PCR fragment," "amplicon" or "amplification product" refer to the resultant mixture of compounds after two or more cycles of the PCR steps of denaturation, annealing and extension are complete. These terms encompass the case where there has been amplification of one or more segments of one or more target sequences.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anti-cancer Drug Des. 8:53 63).

The term "polymerase" refers to an enzyme having the ability to synthesize a complementary strand of nucleic acid from a starting template nucleic acid strand and free dNTPs.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The term "polymerization means" or "polymerization agent" refers to any agent capable of facilitating the addition of nucleoside triphosphates to an oligonucleotide. Preferred polymerization means comprise DNA and RNA polymerases.

As used herein, the terms "oligonucleotide primer pair," "pair of primers," or "primer pair" are used in reference to a composition with a forward primer member and a reverse primer member. The forward primer hybridizes to a sense strand of a target gene sequence to be amplified and primes synthesis of an antisense strand (complementary to the sense strand) using the target sequence as a template. The reverse primer hybridizes to the antisense strand of a target gene sequence to be amplified and primes synthesis of a sense strand (complementary to the antisense strand) using the target sequence as a template.

The primers are configured to bind to conserved sequence regions of a bioagent identifying amplicon that flank an intervening variable region and yield amplification products which provide enough variability to distinguish each individual bioagent, and which are amenable to molecular mass analysis. In some embodiments, the conserved sequence regions exhibit between about 80-100%, or between about 90-100%, or between about 95-100% identity, or between about 99-100% identity. This includes (fractions rounded as described): 80%, 81%, 82%, 83%, 84%, 85%, 86%, 87%, 88%, 89%, 90%, 91%, 92%, 93%, 94%, 95%, 96%, 97%, 98%, 99% or 100%. The molecular mass of a given amplification product provides a means of identifying the bioagent from which it was obtained, due to the variability of the variable region. Thus configuration of the primers requires selection of a variable region with appropriate variability to resolve the identity of a given bioagent. Bioagent identifying amplicons are ideally specific to the identity of the bioagent.

Properties of the primers may include any number of properties related to structure including, but not limited to: nucleobase length which may be contiguous (linked together) or non-contiguous (for example, two or more contiguous segments which are joined by a linker or loop moiety), modified or universal nucleobases (used for specific purposes such as for example, increasing hybridization affinity, preventing non-templated adenylation and modifying molecular mass) percent complementarity to a given target sequences.

Properties of the oligonucleotide primer pairs also include functional features including, but not limited to, orientation of hybridization (forward or reverse) relative to a nucleic acid template. The coding or sense strand is the strand to which the forward priming primer hybridizes (forward priming orientation) while the reverse priming primer hybridizes to the non-coding or antisense strand (reverse priming orientation). The functional properties of a given primer pair also include the generic template nucleic acid to which the primer pair hybridizes. For example, identification of bioagents can be accomplished at different levels using primers suited to resolution of each individual level of identification. Broad range survey primers are configured with the objective of identifying a bioagent as a member of a particular division (e.g., an order, family, genus or other such grouping of bioagents above the species level of bioagents). In some embodiments, broad range survey intelligent primers are capable of identification of bioagents at the species or sub-species level. Other primers may have the functionality of producing bioagent identifying amplicons for members of a given taxonomic genus, lade, species, sub-species or genotype (including genetic variants which may include presence of virulence genes or antibiotic resistance genes or mutations). Additional functional properties of primer pairs include the functionality of performing amplification either singly (single primer pair per amplification reaction vessel) or in a multiplex fashion (multiple primer pairs and multiple amplification reactions within a single reaction vessel).

The term "reference sequence" refers to a fungi bioagent sequence that is used for oligonucleotide primer pair naming. In the preferred embodiment, the nucleic acid sequences from a plurality of fungi bioagents are aligned and conserved regions are identified (as described herein). Primer pairs are configured such that the primer pairs will generate bioagent identifying amplicons from at least two of said plurality of fungi bioagents. One of said plurality of fungi bioagents in the alignment is used as a reference sequence, indicating the position of the primer pair relative to that fungi bioagent. However, the primer pair is not necessarily fully complementary to the reference sequence.

The term "reverse transcriptase" refers to an enzyme having the ability to transcribe DNA from an RNA template. This enzymatic activity is known as reverse transcriptase activity. Reverse transcriptase activity is desirable in order to obtain DNA from RNA viruses which can then be amplified and analyzed by the current methods.

The term "Ribosomal RNA" or "rRNA" refers to the primary ribonucleic acid constituent of ribosomes. Ribosomes are the protein-manufacturing organelles of cells and exist in the cytoplasm. Ribosomal RNAs are transcribed from the DNA genes encoding them.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types. The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is often a contaminant. It may be the result of carryover, or it may be due to the presence of nucleic acid contaminants sought to be purified away from the sample. For example, nucleic acids from organisms other than those to be detected may be present as background in a test sample.

A "segment" or "region" is defined herein as an area of nucleic acid within a larger nucleic acid sequence. Regions are typically called out suing nucleotide numbers of the larger sequence. An example of a region is nucleotides 697 to 1129 of GenBank Accession No.: X70659.1 (gi No.: 671812). Isolated oligonucleotides configured to hybridize within this region are useful for identification of fungi bioagents used the methods described herein. Other examples of regions can include, but are not limited to, exons, genes, VNTRs and conserved regions identified in an alignment of bioagents.

The "self-sustained sequence replication reaction" (3SR) (Guatelli et al., Proc. Natl. Acad. Sci., 87:1874-1878 [1990], with an erratum at Proc. Natl. Acad. Sci., 87:7797 [1990]) is a transcription-based in vitro amplification system (Kwok et al., Proc. Natl. Acad. Sci., 86:1173-1177 [1989]) that can exponentially amplify RNA sequences at a uniform temperature. The amplified RNA can then be utilized for mutation detection (Fahy et al., PCR Meth. Appl., 1:25-33 [1991]). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

As used herein, the term "sequence alignment" refers to a listing of multiple DNA or amino acid sequences and aligns them to highlight their similarities. The listings can be made using bioinformatics computer programs.

As used herein, the term "speciating primer pair" refers to a primer pair configured to produce a bioagent identifying amplicon with the diagnostic capability of identifying species members of a group of genera or a particular genus of bioagents.

As used herein, the term "species confirmation primer pair" refers to a primer pair configured to produce a bioagent identifying amplicon with the diagnostic capability to unambiguously produce a unique base composition to identify a particular species of bioagent.

As used herein, a "sub-species characteristic" is a genetic characteristic that provides the means to distinguish two members of the same bioagent species. For example, one fungal strain could be distinguished from another fungal strain of the same species by possessing a genetic change (e.g., for example, a nucleotide deletion, addition or substitution) in one of the fungal genes, such as the large subunit ribosomal RNA.

As used herein, the term "target," refers to a nucleic acid sequence or structure to be detected or characterized. Thus, the "target" is sought to be sorted out from other nucleic acid sequences and contains a sequence that has at least partial complementarity with an oligonucleotide primer. The target nucleic acid may comprise single- or double-stranded DNA or RNA. A "segment" is defined as a region of nucleic acid within the target sequence.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As used herein, the term "T.sub.m" is used in reference to the "melting temperature." The melting temperature is the temperature at which a population of double-stranded nucleic acid molecules becomes half dissociated into single strands. Several equations for calculating the T.sub.m of nucleic acids are well known in the art. As indicated by standard references, a simple estimate of the T.sub.m value may be calculated by the equation: T.sub.m=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of T.sub.m.

The term "triangulation genotyping analysis" refers to a method of genotyping a bioagent by measurement of molecular masses or base compositions of amplification products, corresponding to bioagent identifying amplicons, obtained by amplification of regions of more than one gene. In this sense, the term "triangulation" refers to a method of establishing the accuracy of information by comparing three or more types of independent points of view bearing on the same findings. Triangulation genotyping analysis carried out with a plurality of triangulation genotyping analysis primers yields a plurality of base compositions that then provide a pattern or "barcode" from which a species type can be assigned. The species type may represent a previously known sub-species or strain, or may be a previously unknown strain having a specific and previously unobserved base composition barcode indicating the existence of a previously unknown genotype.

As used herein, the term "triangulation genotyping analysis primer pair" is a primer pair configured to produce bioagent identifying amplicons for determining species types in a triangulation genotyping analysis.

The employment of more than one bioagent identifying amplicon for identification of a bioagent is herein referred to as "triangulation identification." Triangulation identification is pursued by analyzing a plurality of bioagent identifying amplicons selected within multiple core genes. This process is used to reduce false negative and false positive signals, and enable reconstruction of the origin of hybrid or otherwise engineered bioagents. For example, identification of the three part toxin genes typical of B. anthracis (Bowen et al., J. Appl. Microbiol., 1999, 87, 270-278) in the absence of the expected signatures from the B. anthracis genome would suggest a genetic engineering event.

As used herein, the term "unknown bioagent" may mean either: (i) a bioagent whose existence is known (such as the well known bacterial species Staphylococcus aureus for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. Patent Application Publication No.: US2005-0266397 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. Patent Application Publication No.: US2005-0266397 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

The term "variable sequence" as used herein refers to differences in nucleic acid sequence between two nucleic acids. For example, the genes of two different bacterial species may vary in sequence by the presence of single base substitutions and/or deletions or insertions of one or more nucleotides. These two forms of the structural gene are said to vary in sequence from one another. As used herein, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

The term "virus" refers to obligate, ultramicroscopic, parasites incapable of autonomous replication (i.e., replication requires the use of the host cell's machinery). Viruses can survive outside of a host cell but cannot replicate.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, a "wobble base" is a variation in a codon found at the third nucleotide position of a DNA triplet. Variations in conserved regions of sequence are often found at the third nucleotide position due to redundancy in the amino acid code.

DETAILED DESCRIPTION OF EMBODIMENTS

A. Bioagent Identifying Amplicons

Provided are methods for detection and identification of unknown bioagents using bioagent identifying amplicons. Primers are selected to hybridize to conserved sequence regions of nucleic acids derived from a bioagent, and which bracket variable sequence regions to yield a bioagent identifying amplicon, which can be amplified and which is amenable to molecular mass determination. The molecular mass then provides a means to uniquely identify the bioagent without a requirement for prior knowledge of the possible identity of the bioagent. The molecular mass or corresponding base composition signature of the amplification product is then matched against a database of molecular masses or base composition signatures. The molecular masses or base compositions in a database are indexed to a bioagent and a primer pair. The primer pair corresponds with the primer pair that is used experimentally in the identification methods. Therefore, experimentally derived molecular mass or base composition calculated therefrom, is queried across the database's molecular masses or base compositions indexed to the primer pair until a match is identified. Once a match is identified the fungi bioagent is identified as being that indexed to said database's molecular mass or base composition. The experimentally-determined molecular mass or base composition may be within experimental error of the molecular mass or base composition of a known bioagent identifying amplicon and still be classified as a match. Moreover, if an absolute match is not identified in the database, the fungi bioagent can still be identified using probability cloud, nearest neighbor and/or triangulation, as described herein and in U.S. Patent Application No.: US2006-0259249, which is commonly owned and incorporated herein by reference in entirety. The present method provides rapid throughput and does not require nucleic acid sequencing of the amplified target sequence for bioagent detection and identification.

Despite enormous biological diversity, all forms of life on earth share sets of essential, common features in their genomes. Since genetic data provide the underlying basis for identification of bioagents by the current methods, it is necessary to select segments of nucleic acids which ideally provide enough variability to distinguish each individual bioagent and whose molecular mass is amenable to molecular mass determination.

In some embodiments, at least one fungal nucleic acid segment is amplified in the process of identifying the bioagent. Thus, the nucleic acid segments that can be amplified by the primers disclosed herein and that provide enough variability to distinguish each individual fungal bioagent and whose molecular masses are amenable to molecular mass determination are herein described as fungal bioagent identifying amplicons or fungal identifying amplicons.

In some embodiments, bioagent identifying amplicons comprise from about 45 to about 200 linked nucleosides, or any range therein. One of ordinary skill in the art will appreciate that this embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 nucleobases in length.

It is the combination of the portions of the bioagent nucleic acid segment to which the primers hybridize (hybridization sites) and the variable region between the primer hybridization sites that comprises the bioagent identifying amplicon.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with restriction enzymes or cleavage primers, for example. Thus, in some embodiments, bioagent identifying amplicons are larger than about 200 nucleobases and are amenable to molecular mass determination following restriction digestion or other fragmentation means such as chemical cleavage agents. Methods of using restriction enzymes and cleavage primers are well known to those with ordinary skill in the art. Additionally, mass tags or nucleotide analogs are used.

In some embodiments, amplification products corresponding to bioagent identifying amplicons are obtained using the polymerase chain reaction (PCR) that is a routine method to those with ordinary skill in the molecular biology arts. Other amplification methods may be used such as ligase chain reaction (LCR), low-stringency single primer PCR, and multiple strand displacement amplification (MDA). These methods are also known to those with ordinary skill.

B. Oligonucleotide Primer Pairs and Forward and Reverse Primer Members

As stated above, the primer members are configured to bind to conserved sequence regions of a bioagent identifying amplicon that flank an intervening variable region and yield amplification products which provide variability sufficient to distinguish each individual bioagent, and which are amenable to molecular mass analysis. The molecular mass of a given amplification product provides a means of identifying the bioagent from which it was obtained, due to the variability of the variable region. Thus, configuration of the primers involves, amongst other things, selection of a variable region with sufficient variability to resolve the identity of a given bioagent. In some embodiments, bioagent identifying amplicons are specific to the identity of the bioagent.

In some embodiments, identification of bioagents is accomplished at different levels using primers suited to resolution of each individual level of identification. Broad range survey primers are configured with the objective of identifying a bioagent as a member of a particular division (e.g., an order, family, genus or other such grouping of bioagents above the species level of bioagents). Drill-down primers are configured with the objective of identifying a bioagent at the sub-species level (including strains, subtypes, variants and isolates) based on sub-species characteristics. In some cases, the molecular mass or base composition of a fungal bioagent identifying amplicon defined by a broad range survey primer pair does not provide enough resolution to unambiguously identify a fungal bioagent at or below the species level. These cases benefit from further analysis of one or more fungal bioagent identifying amplicons generated from at least one additional broad range survey primer pair or from at least one additional division-wide primer pair. The employment of more than one bioagent identifying amplicon for identification of a bioagent is herein referred to as triangulation identification.

In one embodiment, the method identifies a species of fungus or a sub-species of fungus.

A preferred embodiment provides isolated oligonucleotide primer pairs wherein each of the forward member and reverse member of the primer pair is independently 13-35 consecutive nucleobases in length and configured to hybridize with at least 70% complementarity to a region of GenBank Accession Number X70659. In a further embodiment, said region is from nucleobase 134 to nucleobase 269. In a further embodiment, said region is from nucleobase 697 to nucleobase 1132. In an alternative embodiment, said region is from nucleobase 697 to nucleobase 834. In an alternative embodiment, said region is from nucleobase 2472 to nucleobase 2624. An additional embodiment provides isolated oligonucleotide primer pairs wherein each of the forward member and reverse member of the primer pair is independently 13-35 consecutive nucleobases in length and configured to hybridize with at least 70% complementarity to a region of GenBank Accession Number X53497. Primer pairs are preferably configured to generate amplification product that comprises a length from 45-200 consecutive nucleobases.

A representative process flow diagram used for primer selection and validation process is outlined in FIG. 1. For each group of organisms, candidate target sequences are identified (200) from which nucleotide alignments are created (210) and analyzed (220). Primers are then configured by selecting appropriate priming regions (230) to facilitate the selection of candidate primer pairs (240). The primer pairs are then subjected to in silico analysis by electronic PCR (ePCR) (300) wherein bioagent identifying amplicons are obtained from sequence databases such as GenBank or other sequence collections (310) and checked for specificity in silico (320). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by testing their ability to hybridize to target nucleic acid by an in vitro amplification by a method such as PCR analysis (400) of nucleic acid from a collection of organisms (410). Amplification products thus obtained are analyzed by gel electrophoresis or by mass spectrometry to confirm the sensitivity, specificity and reproducibility of the primers used to obtain the amplification products (420).

Many of the important pathogens, including the organisms of greatest concern as biowarfare agents, have been completely sequenced. This effort has greatly facilitated the design of primers for the detection of unknown bioagents. The combination of broad-range priming with division-wide and drill-down priming has been used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

In some embodiments, primers are employed as compositions for use in methods for identification of fungal bioagents as follows: a primer pair composition is contacted with nucleic acid of an unknown fungal bioagent. The nucleic acid is then amplified by a nucleic acid amplification technique, such as PCR for example, to obtain an amplification product that represents a bioagent identifying amplicon. The molecular mass of each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known fungi. A match between the molecular mass or base composition of the amplification product and the molecular mass or base composition of an analogous bioagent identifying amplicon for a known fungal bioagent indicates the identity of the unknown bioagent. In some embodiments, the primer pair used is one of the primer pairs of Table 2. In some embodiments, the method is repeated using a different primer pair to resolve possible ambiguities in the identification process or to improve the confidence level for the identification assignment.

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce bioagent identifying amplicons can be accomplished by one with ordinary skill in the art without undue experimentation.

In some embodiments, the oligonucleotide primers are broad range survey primers which hybridize to conserved regions of nucleic acid encoding the 23S rRNA gene, 25S rRNA gene or the 18S rRNA gene (or between 80% and 100%, between 85% and 100%, between 90% and 100% or between 95% and 100%) of known fungi and produce bioagent identifying amplicons.

In other embodiments, the oligonucleotide primers are division-wide primers which hybridize to nucleic acid encoding genes of species within a genus of fungi. In other embodiments, the oligonucleotide primers are drill-down primers which enable the identification of sub-species characteristics. Drill down primers provide the functionality of producing bioagent identifying amplicons for drill-down analyses such as strain typing when contacted with nucleic acid under amplification conditions. Identification of such sub-species characteristics is often critical for determining proper clinical treatment of fungal infections. In some embodiments, sub-species characteristics are identified using only broad range survey primers and division-wide and drill-down primers are not used.

In some embodiments, the primers used for amplification hybridize to and amplify genomic DNA, DNA of bacterial plasmids, DNA of DNA viruses or DNA reverse transcribed from RNA of an RNA virus.

In some embodiments, the primers used for amplification hybridize directly to viral RNA and act as reverse transcription primers for obtaining DNA from direct amplification of viral RNA. Methods of amplifying RNA to produce cDNA using reverse transcriptase are well known to those with ordinary skill in the art and can be routinely established without undue experimentation.

In some embodiments, various computer software programs may be used to aid in design of primers for amplification reactions such as Primer Premier 5 (Premier Biosoft, Palo Alto, Calif.) or OLIGO Primer Analysis Software (Molecular Biology Insights, Cascade, Colo.). These programs allow the user to input desired hybridization conditions such as melting temperature of a primer-template duplex for example. In some embodiments, an in silico PCR search algorithm, such as (ePCR) is used to analyze primer specificity across a plurality of template sequences which can be readily obtained from public sequence databases such as GenBank for example. An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs. In some embodiments, the hybridization conditions applied to the algorithm can limit the results of primer specificity obtained from the algorithm. In some embodiments, the melting temperature threshold for the primer template duplex is specified to be 35.deg.C. or a higher temperature. In some embodiments the number of acceptable mismatches is specified to be seven mismatches or less. In some embodiments, the buffer components and concentrations and primer concentrations may be specified and incorporated into the algorithm, for example, an appropriate primer concentration is about 250 nM and appropriate buffer components are 50 mM sodium or potassium and 1.5 mM Mg.sup.2+.

One with ordinary skill in the art will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g., for example, a loop structure or a hairpin structure). Primer members are configured to have 70% or greater complementarity to at least two fungi bioagent nucleic acids in an alignment. Additionally, the primers can be configured to comprise at least 70%, at least 75%, at least 80%, at least 85%, at least 90%, at least 95% or at least 99% sequence identity with any of the primers listed in Table 2. Thus, in some embodiments, an extent of variation of 70% to 100%, or any range therewithin, of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues ($^{18}/_{20}$=0.9 or 90% sequence identity). In another example, a primer 15 nucleobases in length having all residues identical to a 15 nucleobase segment of primer 20 nucleobases in length would have $^{15}/_{20}$=0.75 or 75% sequence identity with the 20 nucleobase primer.

Percent homology, sequence identity or complementarity, can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid is between about 70% and about 75% 80%. In other embodiments, homology, sequence identity or complementarity, is between about 75% and about 80%. In yet other embodiments, homology, sequence identity or complementarity, is at least 85%, at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range therewithin) sequence identity with the primer sequences specifically disclosed herein.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In one embodiment, the primers are at least 13 nucleobases in length. In another embodiment, the primers are less than 36 nucleobases in length.

In some embodiments the primer members of the oligonucleotide primer pair are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin. The present invention contemplates using both longer and shorter primers. Furthermore, the primers may also be linked to one or more other desired moieties, including, but not limited to, affinity groups, ligands, regions of nucleic acid that are not complementary to the nucleic acid to be amplified, labels, etc. Primers may also form hairpin structures. For example, hairpin primers may be used to amplify short target nucleic acid molecules. The presence of the hairpin may stabilize the amplification complex (see e.g., TAQMAN MicroRNA Assays, Applied Biosystems, Foster City, Calif.).

In some embodiments, any oligonucleotide primer pair may have one or both primers with less than 70% sequence homology with a corresponding member of any of the primer pairs of Table 2 if the primer pair has the capability of producing an amplification product corresponding to a bioagent identifying amplicon. In other embodiments, any oligonucleotide primer pair may have one or both primers with a length greater than 35 nucleobases if the primer pair has the capability of producing an amplification product corresponding to a bioagent identifying amplicon.

In some embodiments, the function of a given primer may be substituted by a combination of two or more primers segments that hybridize adjacent to each other or that are linked by a nucleic acid loop structure or linker which allows a polymerase to extend the two or more primers in an amplification reaction.

In some embodiments, the isolated oligonucleotide primer pairs used for obtaining bioagent identifying amplicons are listed in Table 2. In other embodiments, other primer pairs are possible by combining certain members of the forward primers with certain members of the reverse primers. An example can be seen in Table 2 for three primer pair combinations of forward primer 25S_X70659__134__159_F (SEQ ID NO: 8), with the reverse primers 25S_X70659__247__269_F (SEQ ID NO: 22), or 25S_x70659__235__258_F (SEQ ID NO: 23). Arriving at a favorable alternate combination of primers in a primer pair depends upon the properties of the primer pair, most notably the size of the bioagent identifying amplicon that would be produced by the primer pair, which should be between about 45 to about 200 nucleobases in length. Alternatively, a bioagent identifying amplicon longer than about 200 nucleobases in length could be cleaved into smaller segments by cleavage reagents such as chemical reagents, or restriction enzymes, for example.

In some embodiments, the primers are configured to amplify nucleic acid of a bioagent to produce amplification products that can be measured by mass spectrometry and from whose molecular masses candidate base compositions can be readily calculated.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated adenosine residues as a result of the non-specific enzyme activity of Taq polymerase (Magnuson et al., Biotechniques, 1996, 21, 700-709), an occurrence which may lead to ambiguous results arising from molecular mass analysis.

In some embodiments, primers may contain one or more universal bases. Because any variation (due to codon wobble in the $3^{rd}$ position) in the conserved regions among species is likely to occur in the third position of a DNA (or RNA) triplet, oligonucleotide primers can be configured such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-.beta.-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are configured such that the first and second positions of each triplet are occupied by nucleotide analogs that bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484, 908, each of which is commonly owned and incorporated herein by reference in its entirety. Propynylated primers are described in U.S Pre-Grant Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, non-template primer tags are used to increase the melting temperature (T.sub.m) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynyl-2-deoxycytidine or 5-propynyl-2-deoxythymidine (equivalent to 5-propynyl-2-deoxyuridine) residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises .sup.15N or .sup.13C or both .sup.15N and .sup.13C.

In some embodiments, multiplex amplification is performed where multiple bioagent identifying amplicons are amplified with a plurality of primer pairs. The advantages of multiplexing are that fewer reaction containers (for example, wells of a 96- or 384-well plate) are needed for each molecular mass measurement, providing time, resource and cost savings because additional bioagent identification data can be obtained within a single analysis. Multiplex amplification methods are well known to those with ordinary skill and can be developed without undue experimentation. However, in some embodiments, one useful and non-obvious step in selecting a plurality candidate bioagent identifying amplicons for multiplex amplification is to ensure that each strand of each amplification product will be sufficiently different in molecular mass that mass spectral signals will not overlap and lead to ambiguous analysis results. In some embodiments, a 10 Da difference in mass of two strands of one or more amplification products is sufficient to avoid overlap of mass spectral peaks.

In some embodiments, as an alternative to multiplex amplification, single amplification reactions can be pooled before analysis by mass spectrometry. In these embodiments, as for multiplex amplification embodiments, it is useful to select a plurality of candidate bioagent identifying amplicons to ensure that each strand of each amplification product will be sufficiently different in molecular mass that mass spectral signals will not overlap and lead to ambiguous analysis results.

C Determination of Molecular Mass of Bioagent Identifying Amplicons

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for probes, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used can include, but are not limited to, Fourier transform ion cyclotron resonance mass spectrometry (FT-ICR-MS), time of flight (TOF), ion trap, quadrupole, magnetic sector, Q-TOF, and triple quadrupole.

D. Base Compositions of Bioagent Identifying Amplicons

Although the molecular mass of amplification products obtained using intelligent primers provides a means for identification of bioagents, conversion of molecular mass data to a base composition signature is useful for certain analyses. Base composition is defined above as being the number of individual residues in an amplicon (natural and analog). Base composition is independent of the linear arrangement of said individual residues. In some embodiments, a base composition provides an index of a specific organism. Base compositions can be calculated from known sequences of known bioagent identifying amplicons and can be experimentally determined by measuring the molecular mass of a given bioagent identifying amplicon, followed by determination of all possible base compositions which are consistent with the measured molecular mass within acceptable experimental error. The following example illustrates determination of base composition from an experimentally obtained molecular mass of a 46-mer amplification product originating at position 1337 of the 16S rRNA of *Bacillus anthracis*. The forward and reverse strands of the amplification product have measured molecular masses of 14208 and 14079 Da, respectively. The possible base compositions derived from the molecular masses of the forward and reverse strands for the *B. anthracis* products are listed in Table 1.

TABLE 1

Possible Base Compositions for *B. anthracis* 46mer Amplification Product

| Calc. Mass Forward Strand | Mass Error Forward Strand | Base Composition of Forward Strand | Calc. Mass Reverse Strand | Mass Error Reverse Strand | Base Composition of Reverse Strand |
|---|---|---|---|---|---|
| 14208.2935 | 0.079520 | A1 G17 C10 T18 | 14079.2624 | 0.080600 | A0 G14 C13 T19 |
| 14208.3160 | 0.056980 | A1 G20 C15 T10 | 14079.2849 | 0.058060 | A0 G17 C18 T11 |
| 14208.3386 | 0.034440 | A1 G23 C20 T2 | 14079.3075 | 0.035520 | A0 G20 C23 T3 |
| 14208.3074 | 0.065560 | A6 G11 C3 T26 | 14079.2538 | 0.089180 | A5 G5 C1 T35 |
| 14208.3300 | 0.043020 | A6 G14 C8 T18 | 14079.2764 | 0.066640 | A5 G8 C6 T27 |
| 14208.3525 | 0.020480 | A6 G17 C13 T10 | 14079.2989 | 0.044100 | A5 G11 C11 T19 |
| 14208.3751 | 0.002060 | A6 G20 C18 T2 | 14079.3214 | 0.021560 | A5 G14 C16 T11 |
| 14208.3439 | 0.029060 | A11 G8 C1 T26 | 14079.3440 | 0.000980 | A5 G17 C21 T3 |
| 14208.3665 | 0.006520 | A11 G11 C6 T18 | 14079.3129 | 0.030140 | A10 G5 C4 T27 |
| 14208.3890 | 0.016020 | A11 G14 C11 T10 | 14079.3354 | 0.007600 | A10 G8 C9 T19 |
| 14208.4116 | 0.038560 | A11 G17 C16 T2 | 14079.3579 | 0.014940 | A10 G11 C14 T11 |
| 14208.4030 | 0.029980 | A16 G8 C4 T18 | 14079.3805 | 0.037480 | A10 G14 C19 T3 |
| 14208.4255 | 0.052520 | A16 G11 C9 T10 | 14079.3494 | 0.006360 | A15 G2 C2 T27 |
| 14208.4481 | 0.075060 | A16 G14 C14 T2 | 14079.3719 | 0.028900 | A15 G5 C7 T19 |
| 14208.4395 | 0.066480 | A21 G5 C2 T18 | 14079.3944 | 0.051440 | A15 G8 C12 T11 |
| 14208.4620 | 0.089020 | A21 G8 C7 T10 | 14079.4170 | 0.073980 | A15 G11 C17 T3 |
| — | — | — | 14079.4084 | 0.065400 | A20 G2 C5 T19 |
| — | — | — | 14079.4309 | 0.087940 | A20 G5 C10 T13 |

Among the 16 possible base compositions for the forward strand and the 18 possible base compositions for the reverse strand that were calculated, only one pair (shown in bold) are complementary base compositions, which indicates the true base composition of the amplification product. It should be recognized that this logic is applicable for determination of base compositions of any bioagent identifying amplicon, regardless of the class of bioagent from which the corresponding amplification product was obtained.

In some embodiments, assignment of previously unobserved base compositions (also known as "true unknown base compositions") to a given phylogeny can be accomplished via the use of pattern classifier model algorithms. Base compositions, like sequences, vary slightly from strain to strain within species, for example. In some embodiments, the pattern classifier model is the mutational probability model. On other embodiments, the pattern classifier is the polytope model. The mutational probability model and polytope model are both commonly owned and described in U.S. Publication No. US2006-0259249 which is incorporated herein by reference in entirety.

In one embodiment, it is possible to manage this diversity by building "base composition probability clouds" around the composition constraints for each species. This permits identification of organisms in a fashion similar to sequence analysis. A "pseudo four-dimensional plot" can be used to visualize the concept of base composition probability clouds. Optimal primer design requires optimal choice of bioagent identifying amplicons and maximizes the separation between the base composition signatures of individual bioagents. Areas where clouds overlap indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

Provided are bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more BCS indexes become available in base composition databases.

E. Triangulation Identification

In some cases, a molecular mass of a single bioagent identifying amplicon alone does not provide enough resolution to unambiguously identify a given bioagent. The employment of more than one bioagent identifying amplicon for identification of a bioagent is herein referred to as "triangulation identification." Triangulation identification is pursued by determining the molecular masses of a plurality of bioagent identifying amplicons selected within a plurality of housekeeping genes. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids. In other related embodiments, one PCR reaction per well or container may be carried out, followed by an amplicon pooling step wherein the amplification products of different wells are combined in a single well or container which is then subjected to molecular mass analysis. The combination of pooled amplicons can be chosen such that the expected ranges of molecular masses of individual amplicons are not overlapping and thus will not complicate identification of signals.

F. Codon Base Composition Analysis

In some embodiments, one or more nucleotide substitutions within a codon of a gene of an infectious organism confer drug resistance upon an organism which can be determined by codon base composition analysis. The organism can be a bacterium, virus, fungus or protozoan.

In one embodiment, the amplification product containing the codon being analyzed is of a length of about 35 to about 200 nucleobases. The primers employed in obtaining the amplification product can hybridize to upstream and downstream sequences directly adjacent to the codon, or can hybridize to upstream and downstream sequences one or more sequence positions away from the codon. The primers may have at least 70% sequence complementarity with the sequence of the gene containing the codon being analyzed.

In some embodiments, the codon analysis is undertaken for the purpose of investigating genetic disease in an individual. In other embodiments, the codon analysis is undertaken for the purpose of investigating a drug resistance mutation or any other deleterious mutation in an infectious organism such as a bacterium, virus, fungus or protozoan.

In some embodiments, the molecular mass of an amplification product containing the codon being analyzed is measured by mass spectrometry. The mass spectrometry can be either electrospray (ESI) mass spectrometry or matrix-assisted laser desorption ionization (MALDI) mass spectrometry. Time-of-flight (TOF) is an example of one mode of mass spectrometry compatible with the analyses methods.

The methods can also be employed to determine the relative abundance of drug resistant strains of the organism being analyzed. Relative abundances can be calculated from amplitudes of mass spectral signals with relation to internal calibrants. In some embodiments, known quantities of internal amplification calibrants can be included in the amplification reactions and abundances of analyte amplification product estimated in relation to the known quantities of the calibrants.

In some embodiments, upon identification of one or more drug-resistant strains of an infectious organism infecting an individual, one or more alternative treatments can be devised to treat the individual.

G. Determination of the Quantity of a Bioagent

Figure 2:
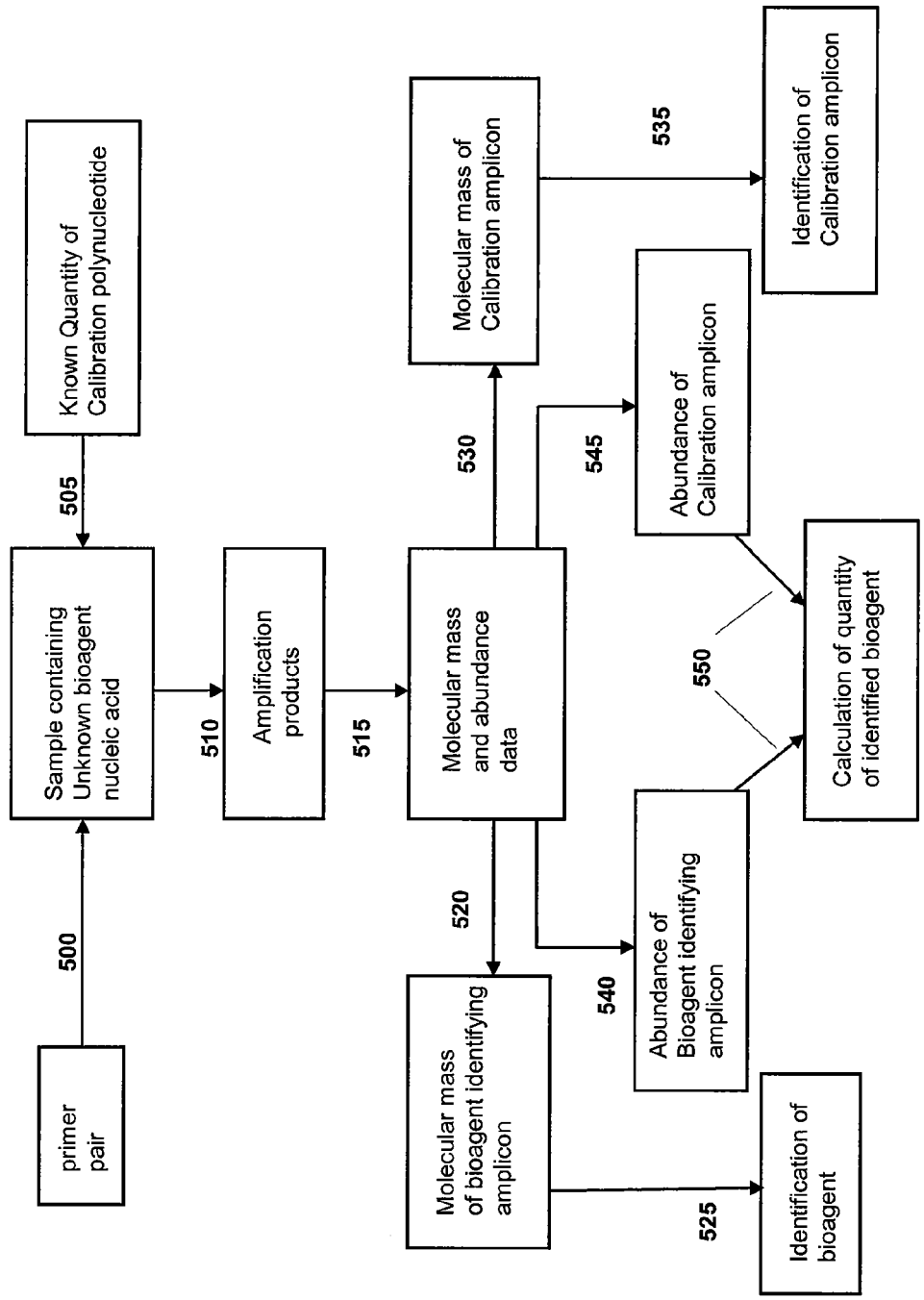
FIG. 2: process diagram illustrating an embodiment of the calibration method.

In some embodiments, the identity and quantity of an unknown bioagent can be determined using the process illustrated in FIG. 2. Primers (500) and a known quantity of a calibration polynucleotide (505) are added to a sample containing nucleic acid of an unknown bioagent. The total nucleic acid in the sample is then subjected to an amplification reaction (510) to obtain amplification products. The molecular masses of amplification products are determined (515) from which are obtained molecular mass and abundance data. The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon is recorded (540) and the abundance data for the calibration data is recorded (545), both of which are used in a calculation (550) which determines the quantity of unknown bioagent in the sample.

A sample comprising an unknown bioagent is contacted with a pair of primers that provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector that itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is configured and used. The process of choosing an appropriate vector for insertion of a calibrant is also a routine operation that can be accomplished by one with ordinary skill without undue experimentation.

H. Identification of Fungi

In certain embodiments, the primer pairs produce bioagent identifying amplicons within stable and conserved regions of fungi. Characterization of an amplicons generated from priming conserved region is preferred because it provides a low probability that the region will evolve past the point of primer recognition, in which case, the amplification step would loose resolution of fungi bioagent and will eventually fail. Such a primer set is thus useful as a broad range survey-type primer. In another embodiment, the primers produce bioagent identifying amplicons in a region which does evolves more quickly than the stable region described above. The advantage of characterization bioagent identifying amplicon corresponding to an evolving genomic region is that it is useful for distinguishing emerging strain variants. In this embodiment the primer pairs are configured to encompass the rapidly evolving region such that the base composition signature for fungi bioagents can be plotted and traced through a phylogenetic tree.

Thus provided is a platform for identification of diseases caused by pathogenic fungi. The present invention eliminates the need for prior knowledge of bioagent sequence to generate hybridization probes because probes are not necessary. Thus, in another embodiment, there is provided a means of determining the etiology of a fungal infection when the process of identification of fungi is carried out in a clinical setting and, even when the fungus is a new species never observed before. This is possible because, as described directly above, the methods are not confounded by naturally occurring evolutionary variations occurring in the sequence acting as the template for production of the bioagent identifying amplicon. Measurement of molecular mass and determination of base composition is accomplished in an unbiased manner without sequence prejudice.

Also provided is a means of tracking the spread of any species or strain of fungus when a plurality of samples obtained from different locations are analyzed by the methods described above in an epidemiological setting. In one embodiment, a plurality of samples from a plurality of different locations is analyzed with primer pairs which produce bioagent identifying amplicons, a subset of which contains a specific fungus. The corresponding locations of the members of the fungus-containing subset indicate the spread of the specific fungus to the corresponding locations.

I. Kits

Also provided are kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pair(s) recited in Table 2.

In some embodiments, the kit comprises one or more broad range survey primer(s), division wide primer(s), or drill-down primer(s), or any combination thereof. If a given problem involves identification of a specific bioagent, the solution to the problem may require the selection of a particular combination of primers to provide the solution to the problem. A kit may be configured so as to comprise particular primer pairs for identification of a particular bioagent. A drill-down kit may be used, for example, to distinguish different subspecies types of fungi. In some embodiments, the primer pair components of any of these kits may be additionally combined to comprise additional combinations of broad range survey primers and division-wide primers so as to be able to identify the fungus.

In some embodiments, the kit contains standardized calibration polynucleotides for use as internal amplification calibrants. Internal calibrants are described in commonly owned International Application WO 2005/094421, which is incorporated herein by reference in its entirety.

In some embodiments, the kit comprises a sufficient quantity of reverse transcriptase (if an RNA virus is to be identified for example), a DNA polymerase, suitable nucleoside triphosphates (including alternative dNTPs such as inosine or modified dNTPs such as the 5-propynyl pyrimidines or any dNTP containing molecular mass-modifying tags such as those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

In some embodiments, the kit includes a computer program stored on a computer formatted medium (such as a compact disk or portable USB disk drive, for example) comprising instructions which direct a processor to analyze data obtained from the use of the primer pairs. The instructions of the software transform data related to amplification products into a molecular mass or base composition which is a useful concrete and tangible result used in identification and/or classification of bioagents. In some embodiments, the kits contain all of the reagents sufficient to carry out one or more of the methods described herein.

While the present compositions and methods has been described with specificity in accordance with certain of its embodiments, the following examples serve only as illustration and are not intended as limitation. It should be understood that these examples are for illustrative purposes only and are not to be construed as limiting in any manner.

Examples

Example 1

Configuration and Validation of Primers that Define Bioagent Identifying Amplicons for Fungi A. General Process of Primer Configuration For configuration of primers that define fungal identifying amplicons, a series of fungal genome segment sequences were obtained, aligned and scanned for regions where pairs of PCR primers would amplify products of about 45 to about 200 nucleotides in length and distinguish species and/or individual strains from each other by their molecular masses or base compositions. A typical process shown in FIG. 1 is employed for this type of analysis.

A database of expected base compositions for each primer region was generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs.

B. Design of Primers for Identification of Fungi

A series of primer pairs (Table 2) have been configured which target ribosomal RNA genes (23S, 25S and 18S) from fungi. The rRNA sequences, obtained from the European Ribosomal Database and public fungal genome sequencing projects, were aligned to each other and to the analogous *Homo sapiens* 5.8 rRNA sequence (GenBank accession #J01866). Primers were selected to specifically exclude amplification of human DNA. Primer pair numbers in Table 2: 3029 (SEQ ID NOs: 9:24), 3030 (SEQ ID NOs: 10:25), 3031 (SEQ ID NOs: 11:26), and 3032 (SEQ ID NOs: 12:27) were compared to the non-redundant GenBank nucleotide database in a theoretical, electronic PCR pre-screening process. Five mismatches were allowed to each primer and a thermodynamic model incorporating base mismatch parameters was utilized to give a global view of phylogenetic specificity and potential cross-reactivity for the four primers. None of the four primers produced a predicted PCR product from any member of the phylum Chordata, suggesting that human and other vertebrate DNAs are not likely to provide a viable template that would inhibit amplification of fungal DNA from clinical specimens.

As a non-limiting example, primer pair number 3030 hybridizes to 25S rRNA and produces amplification products of the following species of fungi: *Candida albicans, Candida dubliniensis, Candida glabrata, Uncinocarpus reesii, Eremothecium gossypii, Saccharomyces cerevisiae, Aspergillus oryzae, Aspergillus fumigatus, Aspergillus terreus, Ajellomyces capsulatus, Neosartorya fischeri, Penicillium verruculosum, Chaetomium globosum, Gibberella moniliformis, Hypocrea jecorina, Verticillium dahliae, Magnaporthe grisea, Symbiotaphrina kochii, Phaeosphaeria nodoru, Lecophagus sp, Botryotinia fuckeliana, Arxula adeninivorans, Saccharomycopsis fibuligera, Schizosaccharomyces japonicus, Schizosaccharomyces pombe, Endogone pisiformis, Tricholoma matsutake, Pneumocystis carinii, Rhizomucor miehei, Mucor racemosus, Rhizopus stolonifer, Endogone lactiflua, Phycomyces blakesleeanus, Cokeromyces recurvatus, Mortierella verticillata, Cryptococcus neoformans, Basidiobolus ranarum, Umbelopsis ramanniana, Mortierella sp., Smittium culisetae, Furculomyces boomerangu, Piptocephalis corymbifera, Kuzuhaea moniliformis, Conidiobolus coronatus, Entomophthora muscae, Dimargaris bacillispora, Orphella haysii, Spiromyces aspiralis, Spiromyces minutus, Coemansia reversa, Rhopalomyces elegans*, and *Bdelloura candida*.

Table 2 represents a collection of primers (sorted by primer pair number) configured to identify fungi using the methods described herein. Tp represents propynylated T and Cp represents propynylated Cp, wherein the propynyl substituent is located at the 5-position of the pyrimidine nucleobase. The primer pair number is an in-house database index number. The forward or reverse primer name shown in Table 2 indicates the gene region of the fungal genome to which the primer hybridizes relative to a reference sequence. The forward primer name 25SCANDIDA_X7 0659_996_1022_F indicates that the forward primer (_F) hybridizes to residues 996-1022 of a reference 25S rRNA *Candida* sequence (GenBank Accession Number X70659). GenBank Accession number X53497 (*Candida albicans* 16S rRNA) is also used for primer configuration. It is notable that the gene nomenclature used is consistent with what is reported in GenBank for these accession numbers. However, and as those or ordinary skill in the art know, nomenclature often differs. For instance, the 16S nomenclature used for X53497 is also referred to as 18S. So too is 25S of X70659 also referred to as 23S. These and other ribosomal genes and their nomenclature are known to those ordinarily skilled in the art.

a Bruker Daltonics MicroTOF instrument. The resulting data was analyzed using GenX software (SAIC, San Diego, Calif., and Ibis, Carlsbad, Calif.).

All PCR reactions were assembled in 50 microliter reaction volumes in a 96-well microtiter plate format using a Packard MPII liquid handling robotic platform and M.J. Dyad thermocyclers (MJ research, Waltham, Mass.). The

TABLE 2

Primer Pairs for Identification of Fungi

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 884 | 16S_X53497_1490_1516_F | TCGAGGTCTGGGTAATCTTGTGAAACT | 1 | 18S_X53497_1550_1574_R | TGCGAGGTATTCCTCGTTGAAGAGC | 15 |
| 885 | 16S_X53497_1302_1325_F | TCGATAACGAACGAGACCTTAACC | 2 | 18S_X53497_1392_1417_R | TCCTGTTATTGCCTCAAACTTCCATC | 16 |
| 886 | 16S_X53497_1298_1323_F | TGCTGCGATAACGAACGAGACCTTAA | 3 | 18S_X53497_1398_1423_R | TCACAGACCTGTTATTGCCTCAAACT | 17 |
| 887 | 16S_X53497_236_262_F | TCCCGGGTGATTCATAATAACTTCTCG | 4 | 18S_X53497_328_350_R | TGCGACCATGGTAGGCCTCTATC | 18 |
| 888 | 25S_X70659_2472_2496_F | TTGTAGAATAAGTGGGAGCTTCGGC | 5 | 25S_X70659_2600_2624_R | TTCCCCACCTGACAATGTCTTCAAC | 19 |
| 889 | 25S_X70659_2472_2496P_F | TTGTAGAATAAGTGGGAGCTpTpCpGGC | 5 | 25S_X70659_2600_2624P_R | TTCCCCACCTGACAATGTCTpTpCpAAC | 19 |
| 890 | 25S_X70659_966_1022_F | TCTCAGGATAGCAGAAACTCGTATCAG | 6 | 25S_X70659_1108_1132_R | TCGCCCACGTCCAATTAAGTAACAA | 20 |
| 891 | 25S_X70659_698_723_F | TCCGTCTAACATCTATGCGAGTGTTT | 7 | 25S_X70659_807_834_R | TCAGCTATGCTCTTACTCAAATCCATCC | 21 |
| 892 | 25S_X70659_134_159_F | TGTGAAGCGGCAAAAGCTCAAATTTG | 8 | 25S_X70659_247_269_R | TCACGGGATTCTCACCCTCTGTG | 22 |
| 894 | 25S_X70659_134_159_F | TGTGAAGCGGCAAAAGCTCAAATTTG | 8 | 25S_X70659_235_258_R | TCACCCTCTATGACGCCCTATTCC | 23 |
| 893 | 25S_X70659_134_159_F | TGTGAAGCGGCAAAAGCTCAAATTTG | 8 | 25S_X70659_247_269P_R | TCACGGGATTCTCACpCpCpTCTGTG | 22 |
| 895 | 25S_X70659_134_159P_F | TGTGAAGCGGCAAAAGCpTpCpAAATpTpTG | 8 | 25S_X70659_235_258P_R | TCACpCpCpTCTATGACGCCCTATpTpCC | 23 |
| 3029 | 25SCANDIDA_X70659_996_1022_F | TCTCAGGATAGCAGAAGCTCGTATCAG | 9 | 23SCANDIDA_X70659_1104_1129_R | TCCACGTTCAATTAAGCAACAAGGAC | 24 |
| 3030 | 25SFUNG_X70659_134_158_F | TGTGAAGCGGCAAAAGCTCAAATTT | 10 | 23SFUNG_X70659_235_261_R | TTCTCACCCTCTGTGACGGCCTGTTCC | 25 |
| 3031 | 25SFUNG_X70659_697_722_F | TGGAGTCTAACATCTATGCGAGTGTT | 11 | 23SFUNG_X70659_808_834_R | TCAGCTATGCTCTTACTCAAATCCATC | 26 |
| 3032 | 25SFUNG_X70659_2472_2496_F | TTGTAGAATAGGTGGGAGCTTCGGC | 12 | 23SFUNG_X70659_2593_2615_R | TGACAATGTCTTCAACCCGGATC | 27 |

Example 2

Sample Preparation and PCR

Samples were processed to obtain viral genomic material using a QIAGEN QIAMP Virus BIOROBOT MDx Kit. Resulting genomic material was amplified using an Eppendorf thermal cycler and the amplicons were characterized on PCR reaction mixture consisted of 4 units of Amplitaq Gold, 1× buffer II (Applied Biosystems, Foster City, Calif.), 1.5 mM $MgCl_2$, 0.4 M betaine, 800 .micro.M dNTP mixture and 250 nM of each primer. The following typical PCR conditions were used: 95.deg.C. for 10 min followed by 8 cycles of 95.deg.C. for 30 seconds, 48.deg.C. for 30 seconds, and 72.deg.C. 30 seconds with the 48.deg.C. annealing temperature increasing 0.9.deg.C. with each of the eight cycles. The PCR was then continued for 37 additional cycles of 95.deg.C. for 15 seconds, 56.deg.C. for 20 seconds, and 72.deg.C. 20 seconds.

Example 3

Solution Capture Purification of PCR Products for Mass Spectrometry with Ion Exchange Resin-Magnetic Beads For solution capture of nucleic acids with ion exchange resin linked to magnetic beads, 25 .micro.1 of a 2.5 mg/mL suspension of BioClone amine terminated superparamagnetic beads were added to 25 to 50 .micro.1 of a PCR (or RT-PCR) reaction containing approximately 10 µM of a typical PCR amplification product. The above suspension was mixed for approximately 5 minutes by vortexing or pipetting, after which the liquid was removed after using a magnetic separator. The beads containing bound PCR amplification product were then washed three times with 50 mM ammonium bicarbonate/50% MeOH or 100 mM ammonium bicarbonate/50% MeOH, followed by three more washes with 50% MeOH. The bound PCR amplicon was eluted with a solution of 25 mM piperidine, 25 mM imidazole, 35% MeOH which included peptide calibration standards.

Example 4

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz Pentium II data station running Bruker's Xmass software under Windows NT 4.0 operating system. Sample aliquots, typically 15 µl, were extracted directly from 96-well microtiter plates using a CTC HTS PAL autosampler (LEAP Technologies, Carrboro, N.C.) triggered by the FTICR data station. Samples were injected directly into a 10 .micro.1 sample loop integrated with a fluidics handling system that supplies the 100 .micro.1/hr flow rate to the ESI source. Ions were formed via electrospray ionization in a modified Analytica (Branford, Conn.) source employing an off axis, grounded electrospray probe positioned approximately 1.5 cm from the metallized terminus of a glass desolvation capillary. The atmospheric pressure end of the glass capillary was biased at 6000 V relative to the ESI needle during data acquisition. A counter-current flow of dry $N_2$ was employed to assist in the desolvation process. Ions were accumulated in an external ion reservoir comprised of an rf-only hexapole, a skimmer cone, and an auxiliary gate electrode, prior to injection into the trapped ion cell where they were mass analyzed. Ionization duty cycles greater than 99% were achieved by simultaneously accumulating ions in the external ion reservoir during ion detection. Each detection event consisted of 1M data points digitized over 2.3 s. To improve the signal-to-noise ratio (S/N), 32 scans were co-added for a total data acquisition time of 74 s.

The ESI-TOF mass spectrometer is based on a Bruker Daltonics MicroTOF.sup.™ device (Bruker Daltonics, Billerica, Mass.). Ions from the ESI source undergo orthogonal ion extraction and are focused in a reflectron prior to detection. The TOF and FTICR are equipped with the same automated sample handling and fluidics described above. Ions are formed in the standard MicroTOF.sup.™ ESI source that is equipped with the same off-axis sprayer and glass capillary as the FTICR ESI source. Consequently, source conditions were the same as those described above. External ion accumulation was also employed to improve ionization duty cycle during data acquisition. Each detection event on the TOF was comprised of 75,000 data points digitized over 75 .micro.s.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer was injected at a high flow rate to rinse the transfer line and spray needle to avoid sample contamination/carryover. Following the rinse step, the autosampler injected the next sample and the flow rate was switched to low flow. Following a brief equilibration delay, data acquisition commenced. As spectra were co-added, the autosampler continued rinsing the syringe and picking up buffer to rinse the injector and sample transfer line. In general, two syringe rinses and one injector rinse were required to minimize sample carryover. During a routine screening protocol a new sample mixture was injected every 106 seconds. More recently a fast wash station for the syringe needle has been implemented which, when combined with shorter acquisition times, facilitates the acquisition of mass spectra at a rate of just under one spectrum/minute.

Raw mass spectra were post-calibrated with an internal mass standard and deconvoluted to monoisotopic molecular masses. Unambiguous base compositions were derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in International Application WO 2005/094421, which is incorporated herein by reference in entirety.

Example 5

De Novo Determination of Base Composition of Amplification Products Using Molecular Mass Modified Deoxynucleotide Triphosphates Because the molecular masses of the four natural nucleobases have a relatively narrow molecular mass range (A=313.058, G=329.052, C=289.046, T=304.046—See Table 3), a persistent source of ambiguity in assignment of base composition can occur as follows: two nucleic acid strands having different base composition may have a difference of about 1 Da when the base composition difference between the two strands is G↔A (−15.994) combined with C↔T (+15.000). For example, one 99-mer nucleic acid strand having a base composition of A27 G30 C21 T21 has a theoretical molecular mass of 30779.058 while another 99-mer nucleic acid strand having a base composition of A26 G31 C22 T20 has a theoretical molecular mass of 30780.052. A 1 Da difference in molecular mass may be within the experimental error of a molecular mass measurement and thus, the relatively narrow molecular mass range of the four natural nucleobases imposes an uncertainty factor. The 1 Da uncertainty factor is eliminated through amplification of a nucleic acid with one mass-tagged nucleobase and three natural nucleobases.

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G↔A combined with C↔T event (Table 3). Thus, the same the G↔A (−15.994) event combined with 5-odo-C↔T (−110.900) event would result in a molecular mass difference of 126.894. If the molecular mass of the base composition A27 G30 5-Iodo-C21 T21 (33422.958) is compared with A26 G31 5-Iodo-C22 T20, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is A27 G30 5-Iodo-C21 T21. In contrast, the analogous amplification without the mass tag has 18 possible base compositions.

TABLE 3

Molecular Masses of Natural Nucleobases and the Mass-Modified Nucleobase 5-Iodo-C and Molecular Mass Differences Resulting from Transitions

| Nucleobase | Molecular Mass | Transition | Molecular Mass |
| --- | --- | --- | --- |
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Mass spectra of bioagent-identifying amplicons were analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent-identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Base count blurring can be carried out as follows. "Electronic PCR" can be conducted on nucleotide sequences of the desired bioagents to obtain the different expected base counts that could be obtained for each primer pair. See for example, Schuler, *Genome Res.* 7:541-50, 1997. In one illustrative embodiment, one or more spreadsheets, such as Microsoft Excel workbooks contain a plurality of worksheets. First in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet, "Sheet1" that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains. One of ordinary skill in the art may understand additional pathways for obtaining similar table differences without undo experimentation.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by taking the most abundant strain's base type composition and adding it to the reference set and then the next most abundant strain's base type composition is added until the threshold is met or exceeded. The current set of data was obtained using a threshold of 55%, which was obtained empirically.

For each base count not included in the reference base count set for that bioagent, the script then proceeds to determine the manner in which the current base count differs from each of the base counts in the reference set. This difference may be represented as a combination of substitutions, $Si=Xi$, and insertions, $Ii=Yi$, or deletions, $Di=Zi$. If there is more than one reference base count, then the reported difference is chosen using rules that aim to minimize the number of changes and, in instances with the same number of changes, minimize the number of insertions or deletions. Therefore, the primary rule is to identify the difference with the minimum sum $(Xi+Yi)$ or $(Xi+Zi)$, e.g., one insertion rather than two substitutions. If there are two or more differences with the minimum sum, then the one that will be reported is the one that contains the most substitutions.

Differences between a base count and a reference composition are categorized as one, two, or more substitutions, one, two, or more insertions, one, two, or more deletions, and combinations of substitutions and insertions or deletions. The different classes of nucleobase changes and their probabilities of occurrence have been delineated in U.S. Patent Application Publication No. 2004209260, which is incorporated herein by reference in entirety.

Example 6

Codon Base Composition Analysis—Assay Development

The information obtained by the codon analysis method is base composition. While base composition is not as information-rich as sequence, it can have the same practical utility in many situations. The genetic code uses all 64 possible permutations of four different nucleotides in a sequence of three, where each amino acid can be assigned to as few as one and as many as six codons. Since base composition analysis can only identify unique combinations, without determining the order, one might think that it would not be useful in genetic analysis. However, many problems of genetic analysis start with information that constrains the problem. For example, if there is prior knowledge of the biological bounds of a particular genetic analysis, the base composition may provide all the necessary and useful information. If one starts with prior knowledge of the starting sequence, and is interested in identifying variants from it, the utility of base composition depends upon the codons used an the amino acids of interest.

Analysis of the genetic code reveals three situations, illustrated in Tables 4A-C. In Table 4A, where the leucine codon CTA is comprised of three different nucleotides, each of the nine possible single mutations are always identifiable using base composition alone, and result in either a "silent" mutation, where the amino acid is not changed, or an unambiguous change to another specific amino acid. Irregardless, the resulting encoded amino acid is known, which is equivalent to the information obtained from sequencing. In Table 4B, where two of the three nucleotides of the original codon are the same, there is a loss of information from a base composition measurement compared to sequencing. In this case, three of the nine possible single mutations produce unambiguous amino acid choices, while the other six each produce two indistinguishable options. For example, if starting with the phenylalanine codon TTC, then either one of the two Ts could change to A, and base composition analysis could not distinguish a first position change from a second position change. A first position change of T to A would encode an isoleucine and a second position change of T to A would encode a tyrosine. However no other options are possible and the value of the information would depend upon whether distinguishing an encoded isoleucine from a tyrosine was biologically important. In Table 4C, all three positions have the same nucleotide, and therefore the ambiguity in amino acid identity is increased to three possibilities. Out of 64 codon choices, 20 have three unique nucleotides (as in Table 4A), 40 have two of the same and one different nucleotide (as in Table 4B) and 4 have the same nucleotide in all three positions (as in Table 4C).

TABLE 4A

Wild Type Codon with Three Unique Nucleobases

| Codon Description | Codon(s) | Codon Base Composition | Amino Acid Coded |
|---|---|---|---|
| WILD TYPE CODON | CTA | A1C1T1 | Leu |
| Single Mutation | ATA | A2T1 | Ile |
| Single Mutation | GTA | A1G1T1 | Val |
| Single Mutation | TTA | A1T2 | Leu |
| Single Mutation | CAA | A1C2 | Gln |
| Single Mutation | CGA | A1G1C1 | Arg |
| Single Mutation | CCA | A1C2 | Pro |
| Single Mutation | CTG | G1C1T1 | Leu |
| Single Mutation | CTC | C2T1 | Leu |
| Single Mutation | CTT | C1T2 | Leu |

TABLE 4B

Wild Type Codon with Two Unique Nucleobases

| Codon Description | Codon(s) | Codon Base Composition | Amino Acid Coded |
|---|---|---|---|
| WILD TYPE CODON | TTC | C1T2 | Phe |
| Single Mutations | ATC, TAC | A1C1T1 | Ile, Tyr |
| Single Mutations | GTC, TGC | G1C1T1 | Val, Cys |
| Single Mutations | CTC, TCC | C2T1 | Leu, Ser |
| Single Mutation | TTA | A1T2 | Leu |
| Single Mutation | TTG | G1T2 | Leu |
| Single Mutation | TTT | T3 | Phe |

TABLE 4C

Wild Type Codon Having Three of the Same Nucleobase

| Codon Description | Codon(s) | Codon Base Composition | Amino Acid Coded |
|---|---|---|---|
| WILD TYPE CODON | TTT | T3 | Phe |
| Single Mutations | ATT, TAT, TTA | A1T2 | Ile, Tyr, Leu |
| Single Mutations | GTT, TGT, TTG | G1T2 | Val, Cys, Leu |
| Single Mutations | CTT, TCT, TTC | C1T2 | Leu, Ser, Phe |

Example 7

Identification of Fungi

Figure 3:
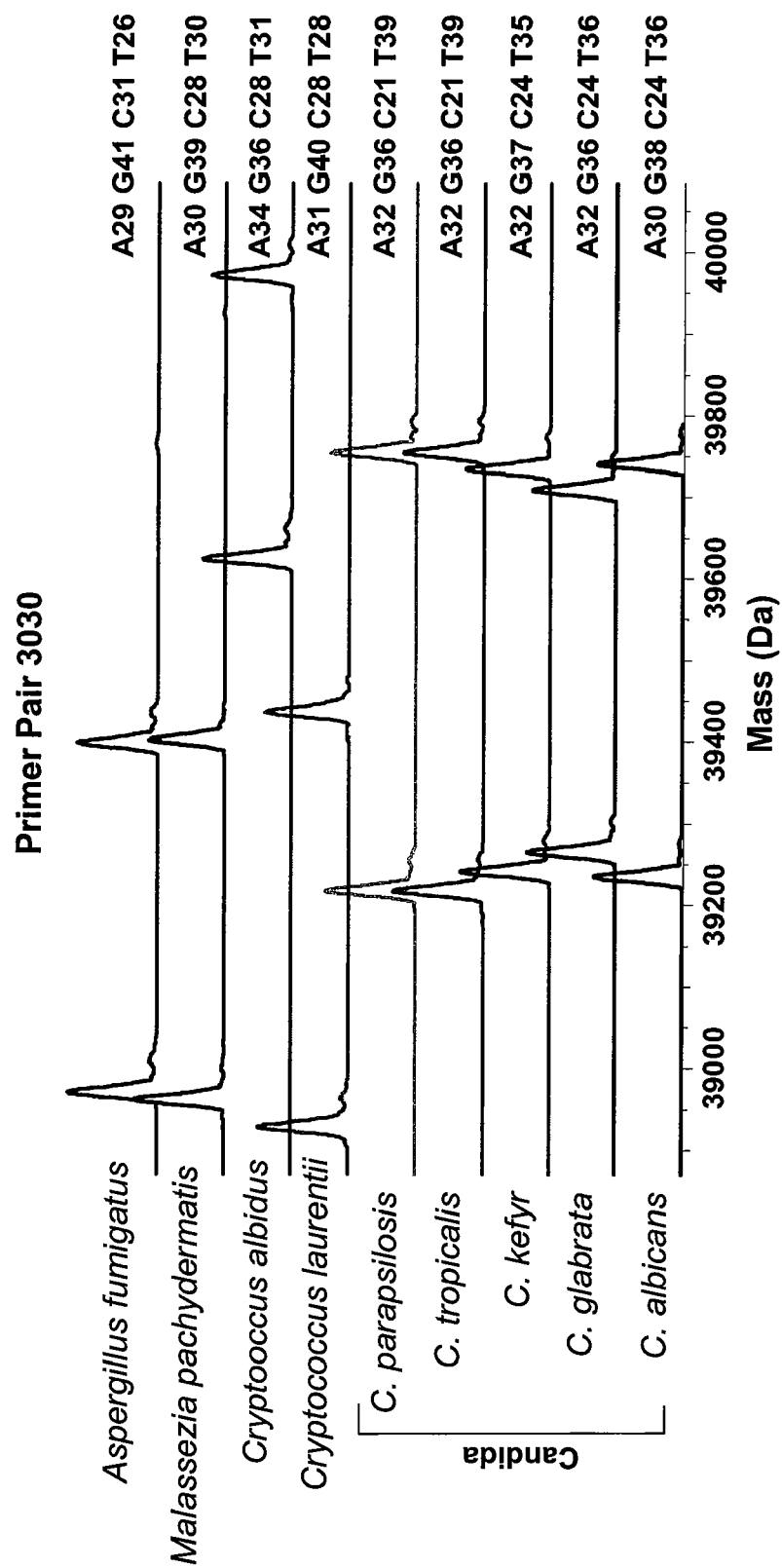
FIG. 3: Series of mass spectra of amplification products of fungi produced with primer pair number 3030 and exhibiting different molecular masses and base compositions.

Primer pair numbers 3029, 3030, 3031 and 3032 were tested in actual PCR reactions using either 500 pg or 50 pg of purified fungal DNA from each of the nine fungal species shown in Tables 5A and 5B. PCR reactions were performed using purified fungal DNA in the presence of 1.6 .micro.g of human DNA (from whole blood) per reaction (an excess ratio of human to fungal DNA of 3200:1 and 32000:1, respectively). Reactions were desalted and analyzed by electrospray mass spectrometry. Resulting masses were compared to a database of molecular masses and corresponding base compositions of fungal bioagent identifying amplicons populated by selection of rRNA nucleic acid segments of fungal species from GenBank. All species were differentiated from one another by their base compositions using any combination of two primer pairs from the group, or primer pair 3032 alone. For example, shown in FIG. 3 are overlaid mass spectra and base compositions of amplification products corresponding to nine fungal bioagent identifying amplicons (base compositions are shown for the sense strand of each amplification product). PCR reactions in the presence of 1.6 .micro.g human DNA yielded results comparable to those with fungal DNA alone. Base composition determinations from reactions performed on 50 pg of target DNA were consistent with results obtained with 500 pg of target DNA, both in the absence and presence of human DNA. The ability to amplify and differentiate multiple species from different phyla with a small number of primer pairs in a standardized platform will provide high value in a clinical setting. A typical real-time assay requires a probe to be configured specifically to each specific target species (or isolate in some cases). For example, whereas nine specific probes may be required to differentiate the nine species indicated in Tables 5A and 5B, primer pair 3032 alone, or any combination of two of the other four primer pairs, was found to be sufficient to identify these nine species.

Figure 4:
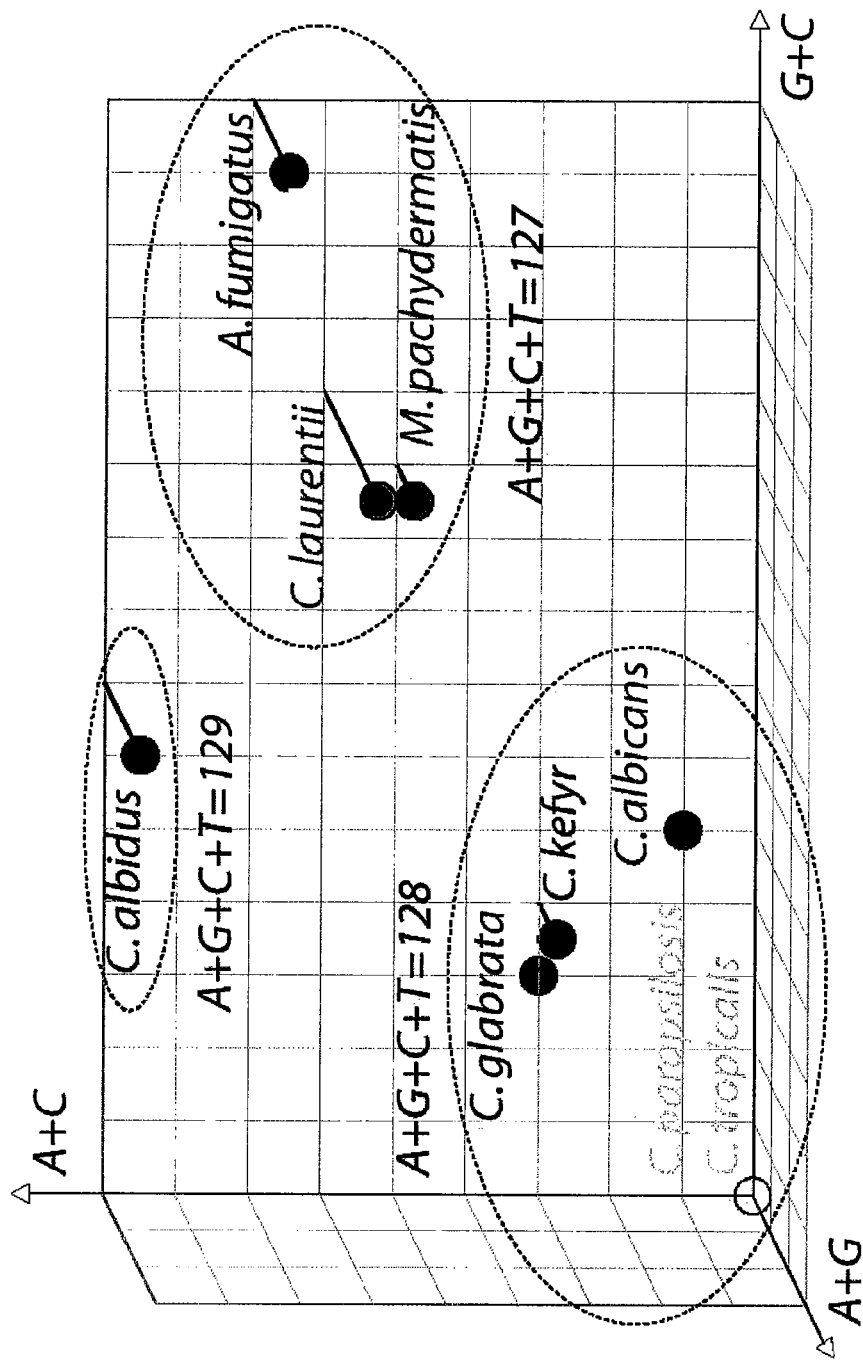
FIG. 4: Three dimensional base composition diagram representing base compositions of amplification products of fungi produced with primer pair number 3030.

It is particularly important to note that it is not necessary that the nucleic acid sequence of the fungus be known in order for an amplification product to be produced and identified as a fungus with similarities to known fungi. For several entries in Tables 5A and 5B, which provides base compositions for nine species of fungi produced with primer pairs 3029, 3030, 3031 and 3032, neither the expected base composition nor primer target site was known directly from sequence data at the time the primers were configured. For example, sequence data was not available for *Candida kefyr*. Provided that enough is known about near neighbors to a target organism, primers that broadly cover members of a phylogenetically-related group of organisms can be configured to generate an amplification product that, once analyzed by mass spectrometry, carries much more information than just the presence or absence of a product. The combination of four base compositions of the amplification products corresponding to bioagent identifying amplicons of *Candida kefyr* obtained using primer pair numbers 3029, 3030, 3031 and 3032 is distinct from the analogous combinations of base compositions of all other species tested, even though the expected compositions from that species were not known beforehand. Thus, the full sequence of a pathogen does not need to be known in order to differentiate it from known organisms using this embodiment. Shown in FIG. 4 is a three dimensional binary base composition diagram indicating binary base compositions for the nine amplification products obtained with primer pair number 3030, which indicates separation of base compositions in three dimensional space.

TABLE 5A

Base Compositions of Fungal Bioagent Identifying Amplicons of Nine Species of Fungi Amplified with Primer Pair Numbers 3029 and 3030

| Fungus | Primer Pair 3029 | Primer Pair 3030 |
| --- | --- | --- |
| Aspergillus fumigatus | not determined | A29 G41 C31 T26 |
| Malassezia pachydermatis | A40 G31 C21 T42 | A30 G39 C28 T30 |
| Cryptococcus albidus | A42 G30 C21 T41 | A34 G36 C28 T31 |
| Cryptococcus laurentii | Did not prime | A31 G40 C28 T28 |
| Candida parapsilosis | A42 G30 C18 T44 | A32 G36 C21 T39 |
| Candida tropicalis | A40 G33 C20 T41 | A32 G36 C21 T39 |
| Candida kefyr | A41 G32 C20 T41 | A32 G37 C24 T35 |
| Candida glabrata | A41 G32 C20 T41 | A32 G36 C24 T36 |
| Candida albicans | A42 G30 C18 T44 | A30 G38 C24 T36 |

TABLE 5B

Base Compositions of Fungal Bioagent Identifying Amplicons of Nine Species of Fungi Amplified with Primer Pair Numbers 3031 and 3032

| Fungus | Primer Pair 3031 | Primer Pair 3032 |
| --- | --- | --- |
| Aspergillus fumigatus | A32 G46 C34 T29 | A31 G38 C35 T44 |
| Malassezia pachydermatis | Did not prime | A30 G41 C35 T42 |
| Cryptococcus albidus | A36 G41 C26 T33 | A32 G38 C32 T46 |
| Cryptococcus laurentii | A37 G41 C25 T33 | A31 G39 C32 T46 |
| Candida parapsilosis | A37 G40 C25 T38 | A34 G39 C30 T42 |
| Candida tropicalis | A34 G44 C25 T35 | A35 G37 C29 T44 |
| Candida kefyr | A36 G43 C25 T34 | A38 G33 C30 T48 |
| Candida glabrata | A34 G45 C28 T37 | A36 G34 C30 T50 |
| Candida albicans | A36 G44 C24 T34 | A35 G37 C31 T41 |

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

While in accordance with the patent statutes, description of the various embodiments and examples have been provided, the scope of the invention is not to be limited thereto or thereby. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

Each reference (including, but not limited to, journal articles, U.S. and non-U.S. patents, patent application publications, international patent application publications, gene bank accession numbers, internet web sites, and the like) cited in the present application is incorporated herein by reference in its entirety.

What is claimed is:

1. A method for identification of a fungus in a sample comprising:
   amplifying nucleic acid from said fungus using an isolated oligonucleotide primer pair wherein the forward member of the primer pair comprises at least 70% sequence identity to SEQ ID NO: 10, and the reverse member of the primer pair is SEQ ID NO: 25 to obtain an amplification product that comprises a length from 45-200 consecutive nucleobases.

2. The method of claim 1 further comprising the step of determining a molecular mass of said amplification product.

3. The method of claim 2 further comprising the step of calculating a base composition from said molecular mass.

4. The method of claim 3 further comprising the step of comparing said calculated base composition with a database of base compositions indexed to primer pairs and known fungi bioagents, wherein a match between said calculated base composition and a base composition in said database indicates the presence of said fungus in said sample.

5. The method of claim 3 further comprising the step of comparing said calculated base composition with a database of base compositions indexed to primer pairs and known fungi bioagents, wherein a match between said calculated base composition and a base composition in said database identifies the species or sub-species of said fungus in said sample.

6. The method of claim 5 wherein said fungus in said sample is identified as a species of fungus or a sub-species of fungus.

7. The method of claim 2 further comprising the step of comparing said determined molecular mass with a database of molecular masses indexed to primer pairs and known fungi bioagents, wherein a match between said determined molecular mass and a molecular mass in said database indicates the presence of said fungus in said sample.

8. The method of claim 2 further comprising the step of comparing said determined molecular mass with a database of molecular masses indexed to primer pairs and known fungi bioagents, wherein a match between said determined molecular mass and a molecular mass in said database identifies the species or sub-species of said fungus in said sample.

9. The method of claim 8 wherein said fungus in said sample is identified as a species of fungus or a sub-species of fungus.

10. The method of claim 9 wherein the fungus in said sample is identified as *Candida albicans, Candida dubliniensis, Candida glabrata, Uncinocarpus reesii, Eremothecium gossypii, Saccharomyces cerevisiae, Aspergillus oryzae, Aspergillus fumigatus, Aspergillus terreus, Ajellomyces capsulatus, Neosartorya fischeri, Penicillium verruculosum, Chaetomium globosum, Gibberella moniliformis, Hypocrea jecorina, Verticillium dahliae, Magnaporthe grisea, Symbiotaphrina kochii, Phaeosphaeria nodoru, Lecophagus* sp, *Bot-*

*ryotinia fuckeliana, Arxula adeninivorans, Saccharomycopsis fibuligera, Schizosaccharomyces japonicus, Schizosaccharomyces pombe, Endogone pisiformis, Tricholoma matsutake, Pneumocystis carinii, Rhizomucor miehei, Mucor racemosus, Rhizopus stolonifer, Endogone lactiflua, Phycomyces blakesleeanus, Cokeromyces recurvatus, Mortierella verticillata, Cryptococcus neoformans, Basidiobolus ranarum, Umbelopsis ramanniana, Mortierella* sp., *Smittium culisetae, Furculomyces boomerangu, Piptocephalis corymbifera, Kuzuhaea moniliformis, Conidiobolus coronatus, Entomophthora muscae, Dimargaris bacillispora, Orphella haysii, Spiromyces aspiralis, Spiromyces minutus, Coemansia reversa, Rhopalomyces elegans*, or *Bdelloura candida*.

11. The method of claim 1 wherein said forward primer member is SEQ ID NO: 10.

12. The method of claim 1 wherein at least one of said forward member and said reverse member comprises at least one modified nucleobase.

13. The method of claim 12 wherein at least one of said at least one modified nucleobase is a mass modified nucleobase.

14. The method of claim 13 wherein said mass modified nucleobase is 5-Iodo-C.

15. The method of claim 13 wherein said mass modified nucleobase comprises a mass modifying tag.

16. The method of claim 12 wherein at least one of said at least one modified nucleobase is a universal nucleobase.

17. The method of claim 16 wherein said universal nucleobase in inosine.

18. The method of claim 1 wherein at least one of said forward member and said reverse member comprises a non-templated T-residue at its 5' end.

19. An isolated oligonucleotide primer pair wherein the forward member of the primer pair with comprises at least 70% sequence identity to SEQ ID NO: 10, and the reverse primer of the primer pair is SEQ ID NO: 25 to obtain an amplification product that comprises a length from 45-200 consecutive nucleobases.

20. The isolated oligonucleotide primer pair of claim 19 wherein said forward primer member is SEQ ID NO: 10.

21. The isolated oligonucleotide primer pair of claim 19 wherein at least one of said forward member and said reverse member comprises at least one modified nucleobase.

22. The isolated oligonucleotide primer pair of claim 21 wherein at least one of said at least one modified nucleobase is a mass modified nucleobase.

23. The isolated oligonucleotide primer pair of claim 22 wherein said mass modified nucleobase is 5-Iodo-C.

24. The isolated oligonucleotide primer pair of claim 22 wherein said mass modified nucleobase comprises a mass modifying tag.

25. The isolated oligonucleotide primer pair of claim 21 wherein at least one of said at least one modified nucleobase is a universal nucleobase.

26. The isolated oligonucleotide primer pair of claim 25 wherein said universal nucleobase in inosine.

27. The isolated oligonucleotide primer pair of claim 19 wherein at least one of said forward member and said reverse member comprises a non-templated T-residue at its 5' end.

* * * * *